(12) United States Patent
Gharib et al.

(10) Patent No.: US 11,033,218 B2
(45) Date of Patent: *Jun. 15, 2021

(54) SYSTEM AND METHODS FOR PERFORMING NEUROPHYSIOLOGIC ASSESSMENTS DURING SPINE SURGERY

(71) Applicant: NuVasive, Inc., San Diego, CA (US)

(72) Inventors: James E. Gharib, San Diego, CA (US); Allen Farquhar, San Diego, CA (US); Doug Layman, San Diego, CA (US)

(73) Assignee: NuVasive, Inc., San Diego, CA (US)

(*) Notice: Subject to any disclaimer, the term of this patent is extended or adjusted under 35 U.S.C. 154(b) by 139 days.

This patent is subject to a terminal disclaimer.

(21) Appl. No.: 16/449,364

(22) Filed: Jun. 22, 2019

(65) Prior Publication Data
US 2019/0307354 A1    Oct. 10, 2019

Related U.S. Application Data

(63) Continuation of application No. 15/645,605, filed on Jul. 10, 2017, now Pat. No. 10,362,957, which is a
(Continued)

(51) Int. Cl.
| | |
|---|---|
| A61B 5/00 | (2006.01) |
| A61B 5/389 | (2021.01) |
| A61N 1/05 | (2006.01) |
| A61N 1/36 | (2006.01) |
| A61N 1/372 | (2006.01) |

(52) U.S. Cl.
CPC .............. *A61B 5/389* (2021.01); *A61B 5/407* (2013.01); *A61B 5/4041* (2013.01); *A61B 5/4504* (2013.01); *A61B 5/4893* (2013.01); *A61B 5/7475* (2013.01); *A61N 1/0548* (2013.01);
(Continued)

(58) Field of Classification Search
CPC ... A61B 5/0488; A61B 5/4893; A61B 5/7475; A61B 5/407; A61B 5/4041; A61B 5/4504; A61N 1/0548; A61N 1/36003; A61N 1/37247
See application file for complete search history.

(56) References Cited

U.S. PATENT DOCUMENTS

| | | |
|---|---|---|
| 2,736,002 A | 2/1956 | Oriel |
| 3,664,329 A | 5/1972 | Naylor |
| (Continued) | | |

FOREIGN PATENT DOCUMENTS

| | | |
|---|---|---|
| WO | 2003005887 A2 | 1/2003 |
| WO | 2003026482 A2 | 4/2003 |
| (Continued) | | |

OTHER PUBLICATIONS

Balzer et al., "Simultaneous somatosensory evoked potential and electromyographic recordings during lumbosacral decompression and instrumentation technique application", Neurosurgery, 1998, pp. 1318-1325, 42, No. 6.
(Continued)

*Primary Examiner* — Scott M. Getzow

(57) ABSTRACT

A system and methods for performing neurophysiologic assessments during surgery, such as assessing the health of the spinal cord via at least one of MEP and SSEP monitoring and assessing bone integrity, nerve proximity, neuromuscular pathway, and nerve pathology during spine surgery.

20 Claims, 36 Drawing Sheets

Related U.S. Application Data continuation of application No. 15/153,703, filed on May 12, 2016, now Pat. No. 9,700,228, which is a continuation of application No. 11/883,709, filed as application No. PCT/US2006/003966 on Feb. 2, 2006, now abandoned.

(60) Provisional application No. 60/719,897, filed on Sep. 22, 2005, provisional application No. 60/649,724, filed on Feb. 2, 2005.

(52) U.S. Cl.
CPC ...... *A61N 1/36003* (2013.01); *A61N 1/37247* (2013.01)

(56) References Cited

U.S. PATENT DOCUMENTS

| | | | |
|---|---|---|---|
| 3,785,368 | A | 1/1974 | McCarthy et al. |
| 4,291,705 | A | 9/1981 | Severinghaus et al. |
| 4,545,374 | A | 10/1985 | Jacobson |
| 4,570,640 | A | 2/1986 | Barsa |
| 4,744,371 | A | 5/1988 | Harris |
| 4,962,766 | A | 10/1990 | Herzon |
| 5,196,015 | A | 3/1993 | Neubardt |
| 5,212,476 | A | 5/1993 | Maloney |
| 5,284,153 | A | 2/1994 | Raymond et al. |
| 5,284,154 | A | 2/1994 | Raymond et al. |
| 5,313,956 | A | 5/1994 | Knutsson et al. |
| 5,474,558 | A | 12/1995 | Neubardt |
| 5,549,656 | A | 8/1996 | Reiss |
| 5,601,608 | A | 2/1997 | Mouchawar |
| 5,775,331 | A | 7/1998 | Raymond et al. |
| 5,779,642 | A | 7/1998 | Nightengale |
| 5,806,522 | A | 9/1998 | Katims |
| 5,810,747 | A | 9/1998 | Brudny et al. |
| 5,830,150 | A | 11/1998 | Palmer et al. |
| 5,830,151 | A | 11/1998 | Hadzic et al. |
| 5,851,191 | A | 12/1998 | Gozani |
| 5,853,373 | A | 12/1998 | Griffith et al. |
| 5,928,158 | A | 7/1999 | Aristides |
| 5,935,131 | A | 8/1999 | Bonutti |
| 6,011,985 | A | 1/2000 | Athan et al. |
| 6,027,456 | A | 2/2000 | Feler et al. |
| 6,038,469 | A | 3/2000 | Karlsson et al. |
| 6,104,957 | A | 8/2000 | Alo et al. |
| 6,132,386 | A | 10/2000 | Gozani et al. |
| 6,132,387 | A | 10/2000 | Gozani et al. |
| 6,224,549 | B1 | 5/2001 | Drongelen |
| 6,259,945 | B1 | 7/2001 | Epstein et al. |
| 6,266,558 | B1 | 7/2001 | Gozani et al. |
| 6,292,701 | B1 | 9/2001 | Prass et al. |
| 6,306,100 | B1 | 10/2001 | Prass |
| 6,334,068 | B1 | 12/2001 | Hacker |
| 6,393,325 | B1 | 5/2002 | Mann et al. |
| 6,416,480 | B1 | 7/2002 | Nenov |
| 6,425,859 | B1 | 7/2002 | Foley et al. |
| 6,451,015 | B1 | 9/2002 | Rittman, III et al. |
| 6,466,817 | B1 | 10/2002 | Kaula et al. |
| 6,564,078 | B1 | 5/2003 | Marino et al. |
| 6,819,956 | B2 | 11/2004 | DiLorenzo |
| 6,830,051 | B1 | 12/2004 | Lesniak et al. |
| 6,895,280 | B2 | 5/2005 | Meadows et al. |
| 6,926,728 | B2 | 8/2005 | Zucherman et al. |
| 7,089,059 | B1 | 8/2006 | Pless |
| 7,207,949 | B2 | 4/2007 | Miles et al. |
| 7,216,001 | B2 | 5/2007 | Hacker et al. |
| 7,470,236 | B1 | 12/2008 | Kelleher et al. |
| 7,522,953 | B2 | 4/2009 | Kaula et al. |
| 7,657,308 | B2 | 2/2010 | Miles et al. |
| 7,664,544 | B2 | 2/2010 | Miles et al. |
| 7,905,840 | B2 | 3/2011 | Pimenta et al. |
| 7,963,927 | B2 | 6/2011 | Kelleher et al. |
| 8,068,912 | B2 | 11/2011 | Kaula et al. |
| 2001/0039949 | A1 | 11/2001 | Loubser |
| 2002/0007129 | A1 | 1/2002 | Marino |
| 2002/0072686 | A1 | 6/2002 | Hoey et al. |
| 2002/0183647 | A1 | 12/2002 | Gozani et al. |
| 2004/0199084 | A1 | 10/2004 | Kelleher et al. |
| 2005/0004623 | A1 | 1/2005 | Miles et al. |
| 2005/0075578 | A1 | 4/2005 | Gharib et al. |
| 2005/0085743 | A1 | 4/2005 | Hacker et al. |
| 2005/0149035 | A1 | 7/2005 | Pimenta et al. |
| 2005/0159785 | A1 | 7/2005 | Rueter |
| 2005/0182454 | A1 | 8/2005 | Gharib et al. |
| 2006/0166157 | A1 | 7/2006 | Rahman et al. |
| 2008/0064976 | A1 | 3/2008 | Kelleher et al. |
| 2008/0064977 | A1 | 3/2008 | Kelleher et al. |
| 2008/0167574 | A1 | 7/2008 | Farquhar |
| 2009/0018610 | A1 | 1/2009 | Gharib et al. |
| 2009/0177112 | A1 | 7/2009 | Gharib et al. |

FOREIGN PATENT DOCUMENTS

| | | |
|---|---|---|
| WO | 2003037170 A3 | 5/2003 |
| WO | 2003043690 A1 | 5/2003 |
| WO | 2005013805 A2 | 2/2005 |
| WO | 2006042075 A2 | 4/2006 |

OTHER PUBLICATIONS

Banoczi, "Update on anesthetic and metabolic effects during intraoperative neurophysiological monitoring (IONM)", Am J END Technol, 2005, pp. 225-239, 45, No. 4.

Bednarik et al., "The value of somatosensory- and motor-evoked potentials in predicting and monitoring the effect of therapy in spondylotic cervical myelopathy: Prospective randomized study", SPINE, 1999, pp. 1593-1598, 24, No. 15.

Calancie et al., "Stimulus-evoked EMG monitoring during transpedicular lumbosacral spine instrumentation", SPINE, 1994, pp. 2780-2786, 19, No. 24.

Calancie et al., "'Threshold-level' multipulse transcranial electrical stimulation of motor cortex for intraoperative monitoring of spinal motor tracts: Description of method and comparison to somatosensory evoked potential monitoring", J Neurosurg, 1998, pp. 457-470, 88, No. 3.

Calancie et al., "Alarm criteria for motor-evoked potentials: What's wrong with the 'presence-or-absence' approach?", SPINE, 2008, pp. 406-414, 33, No. 4.

Calancie et al., "Threshold-level repetitive transcranial electrical stimulation for intraoperative monitoring of central motor conduction", J Neurosurg: Spine, 2001, pp. 161-168, 95, No. 2.

Chawla et al., "Somatosensory evoked potentials: Clinical applications", Medscape, Available at: <http://emedicine.medscape.com/article/1139393-overview>, Accessed Mar. 5, 2009.

Dawson et al., "Spinal cord monitoring: Results of the Scoliosis Research Society and the European Spinal Deformity Society survey", SPINE, 1991, pp. S361-S364, 16, No. 8 Supplement.

Deletis et al., "Neurophysiological mechanisms underlying motor evoked potentials in anesthetized humans.: Part 1. Recovery time of corticospinal tract direct waves elicited by pairs of transcranial electrical stimuli", Clinical Neurophysiology, 2001, pp. 438-444, 112, No. 3.

Deletis et al., "Neurophysiological mechanisms underlying motor evoked potentials in anesthetized humans.: Part 2. Relationship between epidurally and muscle recorded MEPs in man", Clinical Neurophysiology, 2001, pp. 445-452, 112, No. 3.

Deutsch et al., "Somatosensory evoked potential monitoring in anterior thoracic vertebrectomy", J Neurosurg: Spine, 2000, pp. 155-161, 92, No. 2.

Devlin et al., "Intraoperative neurophysiologic monitoring during spinal surgery", J Am Acad Orthop Surg, 2007, pp. 549-560, 15, No. 9.

Ginsburg et al., "Postoperative paraplegia with preserved intraoperative somatosensory evoked potentials", J Neurosurg, 1985, pp. 296-300, 63, No. 2.

Gokaslan et al., "Intraoperative monitoring of spinal cord function using motor evoked potentials via transcutaneous epidural electrode during anterior cervical spinal surgery", J Spinal Disord, 1997, pp. 299-303, 10, No. 4.

(56) References Cited

OTHER PUBLICATIONS

Gunnarsson et al., "Real-time continuous intraoperative electromyographic and somatosensory evoked potential recordings in spinal surgery: Correlation of clinical and electrophysiologic findings in a prospective, consecutive series of 213 cases", SPINE, 2004, pp. 677-684, 29, No. 6.

Holland et al., "Higher electrical stimulus intensities are required to activate chronically compressed nerve roots: implications for intraoperative electromyographic pedicle screw testing", SPINE, 1998, pp. 224-227, 23, No. 2.

International Search Report for PCT/US00/32329, ISA, dated Apr. 27, 2001, pp. 4.

International Search Report for PCT/US01/18579, ISA, dated Jan. 15, 2002, pp. 3.

International Search Report for PCT/US01/18606, ISA, dated Oct. 18, 2001, pp. 4.

International Search Report for PCT/US02/22247, ISA, dated Mar. 27, 2003, pp. 3.

International Search Report for PCT/US02/30617, ISA, dated Jun. 5, 2003, pp. 2.

International Search Report for PCT/US02/35047, ISA, dated Aug. 11, 2003, pp. 3.

International Search Report for PCT/US03/02056, ISA, dated Aug. 12, 2003, pp. 3.

International Search Report for PCT/US06/03966, ISA, dated Oct. 23, 2006, pp. 1.

International Search Report for PCT/US06/37013, ISA, dated Mar. 19, 2007, pp. 6.

Jones et al., "Two cases of quadriparesis following anterior cervical discectomy, with normal perioperative somatosensory evoked potentials", J Neurol Neurosurg Psychiatry, 2003, pp. 273-276, 74, No. 2.

Kamel et al., "The use of somatosensory evoked potentials to determine the relationship between patient positioning and impending upper extremity nerve injury during spine surgery: A retrospective analysis", Anesth Analg, 2006, pp. 1538-1542, 102, No. 5.

Kombos et al., "Impact of somatosensory evoked potential monitoring on cervical surgery", J Clin Neurophysiol, 2003, pp. 122-128, 20, No. 2.

Kombos, et al., "Monitoring of intraoperative motor evoked potentials to increase the safety of surgery in and around the motor cortex", J Neurosurg, 2001, pp. 608-614, 95, No. 4.

Kraft et al., "Somatosensory evoked potentials: Clinical uses", Muscle Nerve, 1998, pp. 252-258, 21, No. 2.

Langeloo et al., "A new application of TCE-MEP: Spinal cord monitoring in patients with severe neuromuscular weakness undergoing corrective spine surgery", J Spinal Disord, 2001, pp. 445-448, 14, No. 5.

Langeloo et al., "Transcranial electrical motor-evoked potential monitoring during surgery for spinal deformity: A study of 145 patients", SPINE, 2003, pp. 1043-1050, 28, No. 10.

Legatt et al., "Somatosensory evoked potentials: General principles", Medscape, Available at: <http://emedicine.medscape.com/article/1139906-overview>, Accessed Mar. 5, 2009.

MacDonald, "Safety of intraoperative transcranial electrical stimulation motor evoked potential monitoring", J Clin Neurophysiol, 2002, pp. 416-429, 19, No. 5.

More et al., "Cortical evoked potential monitoring during spinal surgery: Sensitivity, specificity, reliability, and criteria for alarm", J Spinal Disord, 1988, pp. 75-80, 1, No. 1.

Nash et al., "Spinal cord monitoring during operative treatment of the spine", Clin Orthop Relat Res, 1977, pp. 100-105, No. 126.

Nuwer et al., "Somatosensory evoked potential spinal cord monitoring reduces neurologic deficits after scoliosis surgery: Results of a large multicenter survey", Electroencephalogr Clin Neurophysiol, 1995, pp. 6-11, 96, No. 1.

Osburn et al., "TCeMEPs offer safe, reliable monitoring of spinal cord motor pathway function during cervical procedures performed for post-traumatic spine injury", 17th Annual Meeting of the American Society of Neurophysiological Monitoring Abstract Presentations, 2006.

Osburn, "A guide to the performance of transcranial electrical motor evoked potentials. Part 1. Basic concepts, recording parameters, special considerations, and application", Am J END Technol, 2006, pp. 98-158, 46, No. 2.

Padberg et al., "Somatosensory- and motor-evoked potential monitoring without a wake-up test during no. idiopathic scoliosis surgery: An accepted standard of care", SPINE, 1998, pp. 1392-1400, 23, No. 12.

Pelosi et al., "Combined monitoring of motor and somatosensory evoked potentials in orthopaedic spinal surgery", Clin Neurophysiol, 2002, pp. 1082-1091, 113, No. 7.

RLN Systems Inc,. "Operators manual neurovision SE nerve locator/monitor", 1999, pp. 22.

Sloan et al., "Anesthesia for intraoperative neurophysiologic monitoring of the spinal cord", J Clin Neurophysiol, 2002, pp. 430-443, 19, No. 5.

Toleikis, "Intraoperative monitoring using somatosensory evoked potentials", J Clin Monit Comput, 2005, pp. 241-258, 19, No. 3.

Watanabe et al., "Transcranial electrical stimulation through screw electrodes for intraoperative monitoring of motor evoked potentials", J Neurosurg, 2004, pp. 155-160, 100, No. 1.

Wiedemayer et al., "False negative findings in intraoperative SEP monitoring: analysis of 658 consecutive neurosurgical cases and review of published reports", J Neurol Neurosurg Psychiatry, 2004, pp. 280-286, 75, No. 2.

Wiedemayer et al., "The impact of neurophysiological intraoperative monitoring on surgical decisions: a critical analysis of 423 cases", J Neurosurg, 2002, pp. 255-262, 96, No. 2.

Zornow et al., "Intraoperative somatosensory evoked responses recorded during onset of the anterior spinal artery syndrome", J Clin Monit, 1989, pp. 243-245, 5, No. 4.

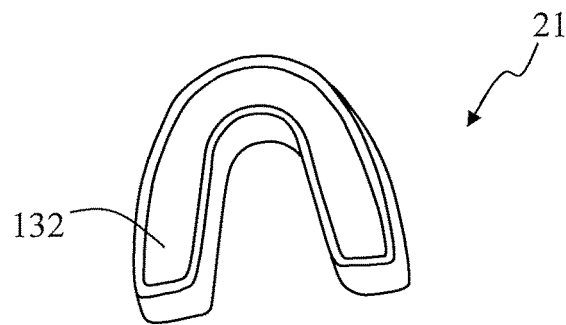
FIG. 13
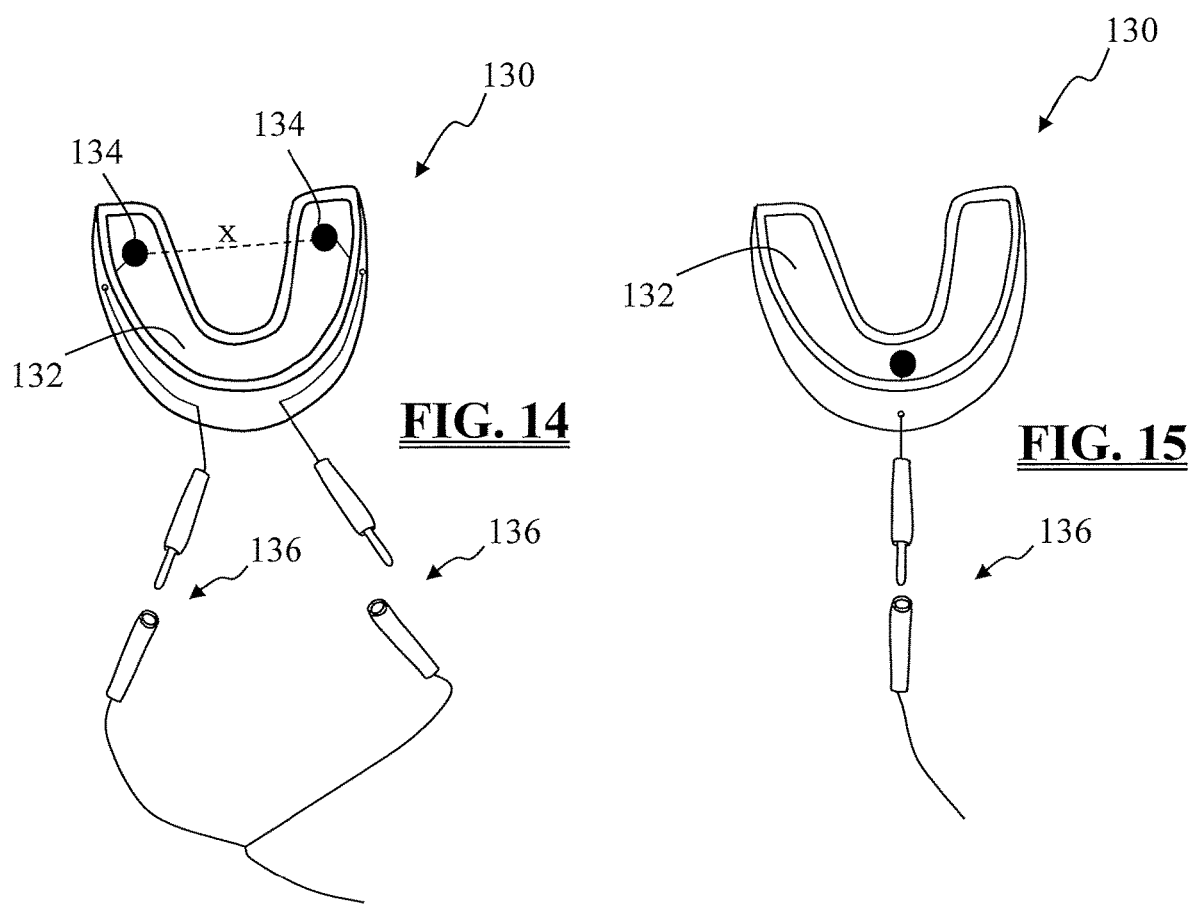
FIG. 14     FIG. 15

LEGEND
*#* = actual recruit
*#̄* = inferred recruit
\# = actual nonrecruit
\#̄ = inferred nonrecruit

NeuroVision JJB® Summary Test Report

| Control Unit Serial Number | Procedure Date: September 24, 2005 |
|---|---|
| | Report Period: 10:30 - 11:24 |

To be completed by Surgeon / OR staff     (use patient label if available)

| Physician_____ | Procedure_____ |
|---|---|
| Patient ID / Medical Record # _____ | |

Procedure Data

Stimulated EMG - Stop on First Response

| Time | Channel/Myotome | Side | Level | Tested | Threshold (mA) |
|---|---|---|---|---|---|
| 11:18:52 | all | Right | L5 | Screw | >20 |
| 11:18:58 | all | Right | L4 | Screw | >20 |
| 11:19:06 | 3 BF Right | Left | L5 | Screw | 17 |
| 11:19:14 | 3 BF Right | Left | L4 | Screw | 19 |

Dynamic EMG

| Time | Channel/Myotome | Side | Level | Tested | Threshold (mA) | Color |
|---|---|---|---|---|---|---|
| 11:17:53 | all | Right | L5 | Pilot Hole | >20 | green |
| 11:18:07 | all | Right | L4 | Pilot Hole | >20 | green |
| 11:18:07 | 3 BF Right | Right | L4 | Pilot Hole | 20 | green |
| 11:18:07 | all | Right | L4 | Pilot Hole | >20 | green |
| 11:18:07 | 3 BF Right | Right | L4 | Pilot Hole | 20 | green |
| 11:18:22 | 3 BF Right | Left | L5 | Pilot Hole | 14 | green |
| 11:18:22 | all | Left | L5 | Pilot Hole | >20 | green |
| 11:18:22 | 3 BF Right | Left | L5 | Pilot Hole | 20 | green |
| 11:18:22 | all | Left | L5 | Pilot Hole | >20 | green |
| 11:18:22 | 3 BF Right | Left | L5 | Pilot Hole | 17 | green |
| 11:18:38 | all | Left | L4 | Pilot Hole | >20 | green |

FIG. 35A

Nerve Detection EMG

| Time | Channel/Myotome | Side | Level | Threshold (mA) | Color |
|---|---|---|---|---|---|
| 10:34:03 | 1 VM Left | Left | N/A | 11 | green |
| 10:34:03 | all | Left | N/A | >20 | green |
| 10:34:03 | 2 TA Right | Left | N/A | 20 | green |
| 10:34:03 | all | Left | N/A | >20 | green |
| 10:34:03 | 3 BF Right | Left | N/A | 15 | green |
| 10:34:03 | 3 BF Right | Left | N/A | 8 | yellow |
| 10:34:03 | 3 BF Left | Left | N/A | 16 | green |
| 11:16:03 | all | Right | L4-L5 | >20 | green |
| 11:16:03 | 3 BF Right | Right | L4-L5 | 20 | green |
| 11:16:03 | all | Right | L4-L5 | >20 | green |
| 11:16:03 | 3 BF Right | Right | L4-L5 | 19 | green |
| 11:16:03 | 3 BF Right | Right | L4-L5 | 5 | yellow |
| 11:16:03 | 3 BF Right | Right | L4-L5 | 12 | green |
| 11:16:03 | all | Right | L4-L5 | >20 | green |
| 11:16:03 | 3 BF Right | Right | L4-L5 | 12 | green |
| 11:16:51 | 3 BF Right | Right | L4-L5 | 16 | green |

Twitch Test

| Time | Channel/Myotome | Ratio |
|---|---|---|
| 10:31:29 | 1 VM Left | >99% |
| 10:35:35 | 3 BF Left | >99% |

Free Run EMG (number of events)

| L.VM | L.TA | L.BF | L.GM | R.VM | R.TA | R.BF | R.GM |
|---|---|---|---|---|---|---|---|
| 1 | | 1 | 1 | 1 | | 4 | 5 |

Total Free Run Time: 41 Minutes
Monitoring time without events at end of case: 0 Minutes

FIG. 35B

Surgeon Operative Notes

Signature                          Date

FIG. 35C

NuVasive Inc. - NeuroVision Test Report

Control Unit Serial Number _____

(use patient label if available)
Physician_____
Patient ID_____
Notes:_____

Procedure Date: September 24, 2005
Report Period: 10:30 - 11:24

Procedure_____

Lumbar Surgery Level(s)

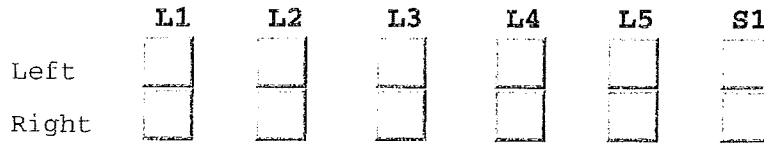

| KEY | | |
|---|---|---|
| Patient's Left and Right | | |
| Channel # | Myotome Group | Spinal Level |
| 1 | Vastus Medialis (VM) | L2, L3, L4 |
| 2 | Tibialis Anterior (TA) | L4, L5 |
| 3 | Biceps Femoris (BF) | L5, S1, S2 |
| 4 | Gastroc. Medial (GM) | S1, S2 |

Testing

Neuromuscular Junction
  # of nerves tested _____

Intraoperative Neurophysiology
Duration: 53 Minutes

Time 10:30:48
Surface electrode channel status
```
        Left 1 VM enabled              Right 1 VM enabled
        Left 2 TA enabled              Right 2 TA enabled
        Left 3 BF enabled              Right 3 BF enabled
        Left 4 GM enabled              Right 4 GM enabled
```

FIG. 36A

```
                          Time 10:31:29
┌ Twitch Test ─────────────────────────────────────────────────────┐
│      Left 1 VM              Direct Stim         13 mA      >99%  │
└──────────────────────────────────────────────────────────────────┘

Time 10:33:26
┌ Free Run EMG     (Vpp readings in microvolts) ───────────────────┐
│  Time     L.VM  L.TA  L.BF  L.GM  R.VM  R.TA  R.BF  R.GM Sensitivity│
│ 10:32:18                     56                       52      50 │
│ 10:33:26  End                                                    │
└──────────────────────────────────────────────────────────────────┘

Time 10:34:03
┌ Nerve Detection EMG Threshold in milliamps ──────────────────────┐
│         Stimulation Site:   Left                                 │
│    Time              Myotome           Threshold        Color    │
│  10:34:06          Left 1 VM            11 mA           green    │
│  10:34:12                              >20 mA           green    │
│  10:34:13          Right 2 TA           20 mA           green    │
│  10:34:13                              >20 mA           green    │
│  10:34:18          Right 3 BF           15 mA           green    │
│  10:34:20          Right 3 BF            8 mA           yellow   │
│  10:34:22          Left 3 BF            16 mA           green    │
│  10:34:27          Detection End                                 │
└──────────────────────────────────────────────────────────────────┘

Time 10:35:35
┌ Twitch Test ─────────────────────────────────────────────────────┐
│      Left 3 BF              Direct Stim         18 mA      >99%  │
└──────────────────────────────────────────────────────────────────┘
```

FIG. 36B

Time 11:15:48

Free Run EMG (Vpp readings in microvolts)

| Time | L.VM | L.TA | L.BF | L.GM | R.VM | R.TA | R.BF | R.GM | Sensitivity |
|---|---|---|---|---|---|---|---|---|---|
| 10:36:10 | | | | | | | 412 | | 50 |
| 10:36:11 | | | | | | | 688 | | 50 |
| 10:36:19 | | | | | | | 268 | | 50 |
| 10:36:19 | | | | | | | | 72 | 50 |
| 10:36:19 | | | | | | | | 988 | 50 |
| 10:36:35 | | | | | | | 68 | | 50 |
| 10:36:36 | | | | | | | | 584 | 50 |
| 10:36:36 | | | | | | | | 780 | 50 |
| 11:10:54 | 56 | | 60 | 108 | | | | | 50 |
| 11:15:48 | End | | | | | | | | |

Time 11:16:03

Nerve Detection EMG Threshold in milliamps
Stimulation Site: Right L4-L5 Dilator

| Time | Myotome | Threshold | Color |
|---|---|---|---|
| 11:16:05 | | >20 mA | green |
| 11:16:05 | Right 3 BF | 20 mA | green |
| 11:16:06 | | >20 mA | green |
| 11:16:12 | Right 3 BF | 19 mA | green |
| 11:16:17 | Right 3 BF | 5 mA | yellow |
| 11:16:21 | Right 3 BF | 12 mA | green |
| 11:16:22 | | >20 mA | green |
| 11:16:25 | Right 3 BF | 12 mA | green |
| 11:16:29 | Detection End | | |

Time 11:16:51

Nerve Detection EMG Threshold in milliamps
Stimulation Site: Right L4-L5 Probe

| Time | Myotome | Threshold | Color |
|---|---|---|---|
| 11:16:54 | Right 3 BF | 16 mA | green |
| 11:17:00 | Detection End | | |

Time 11:17:39

Free Run EMG (Vpp readings in microvolts)

| Time | L.VM | L.TA | L.BF | L.GM | R.VM | R.TA | R.BF | R.GM | Sensitivity |
|---|---|---|---|---|---|---|---|---|---|
| 11:17:39 | End | | | | | | | | |

FIG. 36C

Time 11:17:53

Dynamic EMG Threshold in milliamps
Stimulation Site: Right L5 Pilot Hole

| Left | Myotome | Threshold | Color |
|---|---|---|---|
| 11:17:55 | | >20 mA | green |
| 11:17:59 | Dynamic End | | |

Time 11:18:07

Dynamic EMG Threshold in milliamps
Stimulation Site: Right L4 Pilot Hole

| Left | Myotome | Threshold | Color |
|---|---|---|---|
| 11:18:09 | | >20 mA | green |
| 11:18:09 | Right 3 BF | 20 mA | green |
| 11:18:09 | | >20 mA | green |
| 11:18:10 | Right 3 BF | 20 mA | green |
| 11:18:12 | Dynamic End | | |

Time 11:18:22

Dynamic EMG Threshold in milliamps
Stimulation Site: Left L5 Pilot Hole

| Left | Myotome | Threshold | Color |
|---|---|---|---|
| 11:18:25 | Right 3 BF | 14 mA | green |
| 11:18:28 | | >20 mA | green |
| 11:18:28 | Right 3 BF | 20 mA | green |
| 11:18:28 | | >20 mA | green |
| 11:18:30 | Right 3 BF | 17 mA | green |
| 11:18:31 | Dynamic End | | |

Time 11:18:38

Dynamic EMG Threshold in milliamps
Stimulation Site: Left L4 Pilot Hole

| Left | Myotome | Threshold | Color |
|---|---|---|---|
| 11:18:40 | | >20 mA | green |
| 11:18:42 | Dynamic End | | |

FIG. 36D

Time 11:18:52

Stimulated EMG Threshold in milliamps - Stop on First Response
Stimulation Site: Right L5 Screw

| Left | Threshold | Right | Threshold |
|---|---|---|---|
| 1 VM | >20 | 1 VM | >20 |
| 2 TA | >20 | 2 TA | >20 |
| 3 BF | >20 | 3 BF | >20 |
| 4 GM | >20 | 4 GM | >20 |

Time 11:18:58

Stimulated EMG Threshold in milliamps - Stop on First Response
Stimulation Site: Right L4 Screw

| Left | Threshold | Right | Threshold |
|---|---|---|---|
| 1 VM | >20 | 1 VM | >20 |
| 2 TA | >20 | 2 TA | >20 |
| 3 BF | >20 | 3 BF | >20 |
| 4 GM | >20 | 4 GM | >20 |

Time 11:19:06

Stimulated EMG Threshold in milliamps - Stop on First Response
Stimulation Site: Left L5 Screw

| Left | Threshold | Right | Threshold |
|---|---|---|---|
| 1 VM | >20 | 1 VM | >20 |
| 2 TA | >20 | 2 TA | >20 |
| 3 BF | >20 | 3 BF | 17 |
| 4 GM | >20 | 4 GM | >20 |

Time 11:19:14

Stimulated EMG Threshold in milliamps - Stop on First Response
Stimulation Site: Left L4 Screw

| Left | Threshold | Right | Threshold |
|---|---|---|---|
| 1 VM | >20 | 1 VM | >20 |
| 2 TA | >20 | 2 TA | >20 |
| 3 BF | >20 | 3 BF | 19 |
| 4 GM | >20 | 4 GM | >20 |

FIG. 36E

SYSTEM AND METHODS FOR PERFORMING NEUROPHYSIOLOGIC ASSESSMENTS DURING SPINE SURGERY

CROSS REFERENCE TO RELATED APPLICATIONS

This application is a continuation of, and therefore claims the benefit of and priority to U.S. application Ser. No. 15/645,605, filed Jul. 10, 2017, now pending, which is a continuation of U.S. application Ser. No. 15/153,703, filed May 12, 2016, now U.S. Pat. No. 9,700,228, which is a continuation of, and claimed the benefit of and priority to U.S. application Ser. No. 11/883,709, filed Sep. 5, 2008, now abandoned, which was a National Stage Entry of International Application No. PCT/US2006/003966, filed Feb. 2, 2006, which claimed the benefit of and priority to U.S. Provisional Application No. 60/719,897 filed Sep. 22, 2005 and U.S. Provisional Application No. 60/649,724 filed Feb. 2, 2005. The contents of the prior applications are incorporated by reference in their entirety as a part of this application.

BACKGROUND OF THE INVENTION

I. Field of the Invention

The present invention relates generally to a system and methods for performing neurophysiologic assessments during surgery, such as assessing the health of the spinal cord via at least one of MEP and SSEP monitoring, and assessing at least one of bone integrity, nerve proximity, neuromuscular pathway, and nerve pathology (free-run and evoked) during spine surgery.

II. Discussion of the Prior Art

Surgical procedures conducted on or around the spine can be beneficial in reversing or mitigating a variety of ailments commonly suffered by patients. Despite ongoing advances in surgical methods, however, neurological impairment remains a serious concern during surgical spine procedures. The safety of the spinal cord is of paramount importance because damage to the spinal cord may have devastating results for the patient. Consequences of spinal cord damage may range from a slight loss of sensation to complete paralysis of the extremities, depending on the location and extent of damage. Assessing the spinal cord before, during and/or after surgery can provide the surgeon with valuable information on the health of the cord. Such information may allow the surgeon to initiate corrective measures if the health of the cord is compromised, thereby decreasing the chance of permanent spinal cord damage and the resulting consequences.

The spinal cord is composed of a number of nerve pathways including motor and sensory pathways. Motor pathways transmit signals from the brain to the various muscle groups of the body. Conversely, sensory pathways transmit signals from the skin and other parts of the body up to the brain. Currently, methods exist for assessing the health of the spinal cord by monitoring electrical transmission along these pathways. Degradation of an electrical signal introduced near the origin of a pathway and monitored near the end of the pathway is indicative of damage to the spinal cord.

Motor pathway monitoring may be accomplished by stimulating the motor cortex in the brain and recording the resulting EMG response of various muscles in the upper and lower extremities. This method is referred to as trans-cranial electrical motor evoked potential (tce MEP, or simply "MEP") monitoring.

Sensory pathway monitoring may be accomplished by stimulating a peripheral nerve that enters the spinal cord below the level of surgery and recording the resulting action potentials from electrodes on the scalp or high level cervical vertebra. This method is referred to as somatosensory evoked potential (SSEP) monitoring.

While MEP and SSEP monitoring are generally effective for assessing the health of the spinal cord, data from the current methods is typically received as electrical waveforms that must first be analyzed and interpreted in order to provide meaningful data to the surgeon. Interpreting the data can be a complex and difficult task and typically requires specially trained personnel to complete it. This is disadvantageous in that it increases surgery time (additional time needed to interpret data and communicate significance to the surgeon), translates into extra expense (having extra highly trained persons in attendance), and oftentimes presents scheduling challenges because most hospitals do not retain such specially trained personnel.

Based on the foregoing, a need exists for a better system and methods for monitoring the health of the spinal cord before, during, and or after surgery, and in particular, a need for a system that has the ability to conduct MEP and SSEP monitoring while quickly presenting data to the user in a simplified yet meaningful way. A need also exists for a system for monitoring the health of the spinal cord while providing the ability to assess at least one of bone integrity, nerve proximity, neuromuscular pathway, and nerve pathology (free-run and evoked) during spine surgery.

The present invention is directed at addressing the above identified needs and overcoming, or at least improving upon, the disadvantages of the prior art.

SUMMARY OF THE INVENTION

The present invention includes a system and related methods for performing neurophysiologic assessments during surgery, such as assessing the health of the spinal cord via at least one of MEP and SSEP monitoring, and assessing at least one of bone integrity, nerve proximity, neuromuscular pathway, and nerve pathology (free-run and evoked) during spine surgery.

According to a broad aspect, the present invention includes a surgical system, comprising a control unit and a surgical instrument. The control unit has at least one of computer programmed software, firmware and hardware capable of delivering a stimulation signal, receiving and processing neuromuscular or other bioelectric responses due to the stimulation signal, and identifying a relationship between the neuromuscular response and the stimulation signal. The surgical instrument has at least one stimulation electrode in communication with the control unit (via hardwire or wireless) for transmitting a stimulation signal. The control unit is capable of assessing at least one of spinal cord health via MEP or SSEP monitoring, bone integrity, nerve proximity, and nerve pathology based on the identified relationship between a stimulation signal and a corresponding neuromuscular response.

In a further embodiment of the surgical system of the present invention, the control unit is further equipped to communicate at least one of alpha-numeric and graphical information to a user regarding at least one of MEP, SSEP, bone integrity, nerve proximity, nerve direction, and nerve pathology.

In a further embodiment of the surgical system of the present invention, the hardware employed by the control unit to provide a stimulation signal may comprise an MEP stimulator capable of delivering a range of high voltage, constant current pulses for stimulating the motor cortex through the skull, wherein the control unit assesses the health of the spinal cord based on the identified relationship between the neuromuscular response and the stimulation signal.

In a further embodiment of the surgical system of the present invention, the MEP stimulator may be communicatively linked to the control unit via wireless technology.

In a further embodiment of the surgical system of the present invention, a bite block may be used in conjunction with the MEP stimulator, wherein the bite block is communicatively linked to the system and placement of the bite block may be confirmed by the system prior to MEP stimulation.

In a further embodiment of the present invention, the hardware employed by the control unit to provide a stimulation signal may comprise a patient module capable of delivering a range of low voltage, constant current pulses for stimulating a peripheral nerve, wherein the control unit assess the health of the nerve pathways based on the identified relationship between the stimulation signal and the corresponding neuromuscular response.

In a further embodiment of the present invention, the hardware employed by the control unit to provide a stimulation signal may comprise a patient module capable of delivering a range of low voltage pulses at a constant current (or constant voltage, if desired) for stimulating a nerve, wherein the control unit determines at least one of bone integrity, nerve proximity, nerve direction, and nerve pathology based on the identified relationship between the neuromuscular response and the stimulation signal.

In a further embodiment of the surgical system of the present invention, the surgical instrument may comprise at least one of a device for forming a hole in bone (e.g. for testing pedicle integrity), a device for accessing a surgical target site, and a device for maintaining contact with a nerve during surgery.

In a further embodiment of the surgical system of the present invention, the surgical instrument comprises a screw test instrument, wherein the control unit determines the degree of electrical communication between the screw test instrument and an exiting spinal nerve root to assess whether a pedicle has been breached during at least one of pilot hole formation (e.g. via an awl), pilot hole preparation (e.g. via a tap), and screw placement (e.g. via a ball-tipped probe).

In a further embodiment of the surgical system of the present invention, the surgical instrument comprises a nerve root retractor, wherein the control unit determines nerve pathology based on the identified relationship or change in relationship between the neuromuscular response and the stimulation signal.

In a further embodiment of the surgical system of the present invention, the surgical instrument comprises a dilating instrument, wherein the control unit determines at least one of proximity and direction between a nerve and the instrument based on the identified relationship between the neuromuscular response and the stimulation signal.

In a further embodiment of the surgical system of the present invention, the dilating instrument comprises at least one of a K-wire, an obturator, a dilating cannula, and a working cannula.

In a further embodiment of the surgical system of the present invention, the surgical instrument comprises a tissue retractor assembly and the control unit determines at least one of proximity and direction between a nerve and the instrument based on the identified relationship between the neuromuscular response and the stimulation signal.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 13 is a perspective view of a bite block for use with the present invention;

FIG. 14 is a perspective view of the bite block of FIG. 13 including a pair of electrodes communicatively linked to the system as a means of providing a safety check;

FIG. 15 is a perspective view of the bite block of FIG. 13 including one electrode communicatively linked to the system as a means of providing a safety check;

FIGS. 23-24 are exemplary screen displays illustrating various embodiments of the MEP Automatic mode function according to one aspect of;

FIGS. 35A-35C is an exemplary representation of a summary report according to one embodiment of the present invention; and FIGS. 36A-36E is an exemplary representation of a full report according to one embodiment of the present invention.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems disclosed herein boast a variety of inventive features and components that warrant patent protection, both individually and in combination.

Figure 1:
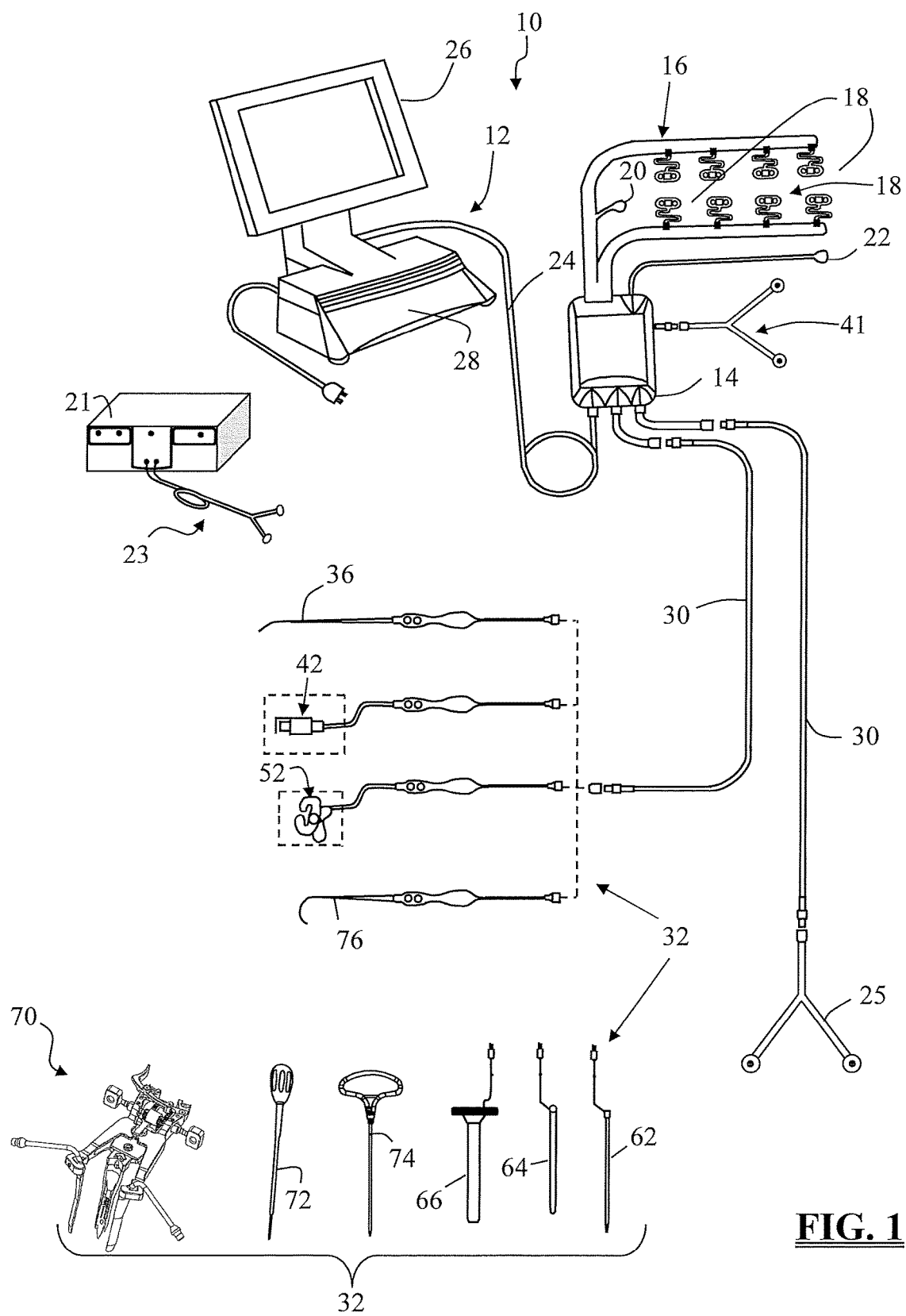
FIG. 1 is a perspective view of an exemplary surgical system 10 capable of conducting multiple nerve and spinal cord monitoring functions including but not necessarily limited to MEP, SSEP, neuromuscular pathway, bone integrity, nerve detection, and nerve pathology (evoked or free-run EMG) assessments.

FIG. 1 illustrates, by way of example only, a surgical system 10 capable of assessing the health of the spinal cord via at least one of MEP and SSEP monitoring and quickly presenting meaningful data to the surgeon. The surgical system 10 is further capable of conducting other neural monitoring functions including, but not necessarily limited to, stimulated EMG, neuromuscular pathway assessments (Twitch Test), pedicle screw testing (Screw Test), nerve proximity monitoring (Detection), and nerve pathology monitoring (Nerve Retractor). It is expressly noted that, although described herein largely in terms of use in spinal surgery, the surgical system 10 and related methods of the present invention are suitable for use in any number of additional procedures, surgical or otherwise, wherein assessing the health of the spinal cord and/or various other nerves may prove beneficial, such as, for example only, when the blood supply to the spinal cord is at risk during thoracic vascular surgery.

The surgical system 10 includes a control unit 12, a patient module 14, an EMG harness 16, including eight pairs of EMG electrodes 18 and a return (anode) electrode 22 coupled to the patient module 14, an MEP stimulator 21, a pair of peripheral nerve stimulation (PNS) electrodes 25 also coupled to the patient module 14, at least one pair of stimulation electrodes 23 coupled to the MEP stimulator 21, and a host of surgical accessories 32 capable of being coupled to the patient module 14 via one or more accessory cables 30. The surgical accessories 32 may include, but are not necessarily limited to, stimulation accessories (such as a screw test probe 36 and dynamic stimulation clips 42, 52), surgical access components (such as a K-wire 62, one or more dilating cannula 64, a working cannula 66, and a tissue retraction assembly 70), and neural pathology monitoring devices (such as a nerve root retractor 76).

Figure 2:
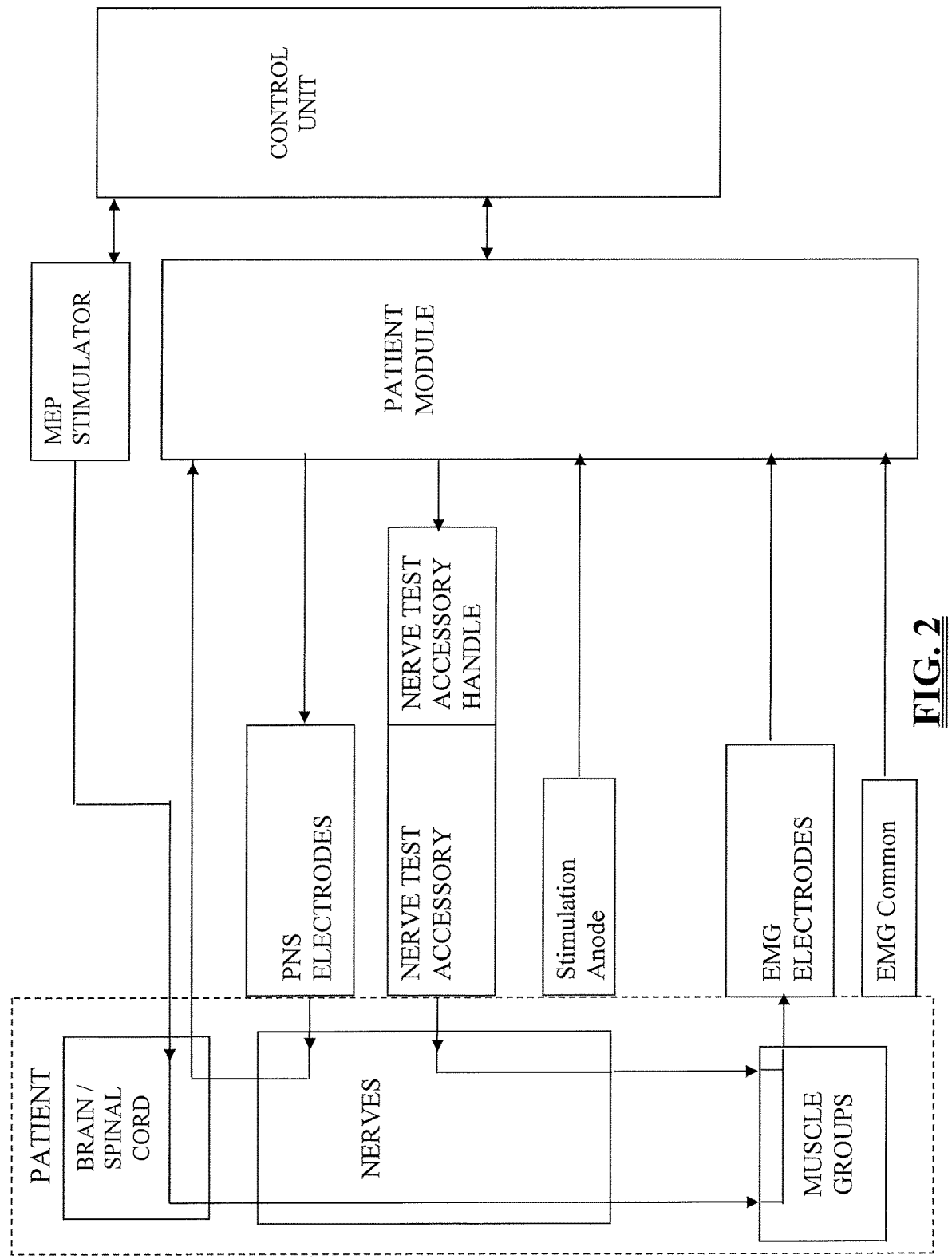
FIG. 2 is a block diagram of the surgical system 10 shown in FIG. 1.

FIG. 2 is a block diagram of the surgical system 10, the operation of which will be explained in conjunction with FIG. 1. The control unit 12 includes a touch screen display 26 and a base 28, which collectively contain the essential processing capabilities for controlling the surgical system 10. The touch screen display 26 is preferably equipped with a graphical user interface (GUI) capable of graphically communicating information to the user and receiving instructions from the user. The base 28 contains computer hardware and software that commands the stimulation sources (e.g. MEP stimulator 21 and patient module 14) receives digital and/or analog signals and other information from the patient module 14, processes the EMG responses, and displays the processed data to the operator via the display 26. The primary functions of the software within the control unit 12 include receiving user commands via the touch screen display 26, activating stimulation in the requested mode (MEP, SSEP, Twitch Test, Screw Test (Basic, Difference, Dynamic), Detection, and Nerve Retractor), processing signal data according to defined algorithms (described below), displaying received parameters and processed data, and monitoring system status.

The patient module 14 is connected via a data cable 24 to the control unit 12, and contains the electrical connections to electrodes, signal conditioning circuitry, stimulator drive and steering circuitry, and a digital communications interface to the control unit 12. In use, the control unit 12 is situated outside but close to the surgical field (such as on a cart adjacent the operating table) such that the display 26 is directed towards the surgeon for easy visualization. The patient module 14 may be located near the patient's legs or may be affixed to the end of the operating table at mid-leg level using a bedrail clamp. The position selected should be such that all EMG electrodes 18 can reach their farthest desired location without tension during the surgical procedure.

The information displayed to the user on the display 26 may include, but is not necessarily limited to, alpha-numeric and/or graphical information regarding any of the requested modes (e.g., MEP, SSEP, Twitch Test, Screw Test (Basic, Difference, Dynamic), Detection, and Nerve Retractor), myotome/EMG levels, stimulation levels, etc . . . In one embodiment, set forth by way of example only, this information may include at least some of the following components (depending on the active mode) as set forth in Table 1:

example only, the Cervical and Thoracolumbar spinal regions may include the Twitch Test, Basic Screw Test, Difference Screw Test, Dynamic Screw Test, MEP Auto, and MEP Manual modes, while the Lumbar spinal region includes the Twitch Test, Basic Screw Test, Difference Screw Test, Dynamic Screw Test, MaXcess® Detection, and Nerve Retractor modes, all of which will be described in greater detail below. (Although not shown, each of the spinal regions may also include an SSEP mode, as will be described in greater detail below.) The Twitch Test mode is designed to assess the neuromuscular pathway via the so-called "train-of-four" test to ensure the neuromuscular pathway is free from muscle relaxants prior to performing neurophysiology-based testing, such as bone integrity (e.g. pedicle) testing, nerve detection, and nerve retraction. This is described in greater detail within Int'l Patent App. No. PCT/US05/36089, entitled "System and Methods for Assessing the Neuromuscular Pathway Prior to Nerve Testing," filed Oct. 7, 2005, the entire contents of which is hereby incorporated by reference as if set forth fully herein. The Basic Screw Test, Difference Screw Test, and Dynamic Screw Test modes are designed to assess the integrity of bone (e.g. the pedicle) during all aspects of pilot hole formation (e.g., via an awl), pilot hole preparation (e.g. via a tap), and screw introduction (during and after). These

TABLE 1

| Screen Component | Description |
| --- | --- |
| Spine Image | An image of the human body/skeleton showing the electrode placement on the body, with labeled channel number tabs on each side (1-4 on the left and right). Left and right labels will show the patient orientation. The channel number tabs may be highlighted or colored depending on the specific function being performed. |
| Myotome & Level Names | A label to indicate the Myotome name and corresponding Spinal Level(s) associated with the channel of interest. |
| Menu | A drop down navigation component for toggling between functions. |
| Display Area | Shows procedure-specific information including stimulation results. |
| Color Indication | Enhances stimulation results with a color display of green, yellow, or red corresponding to the relative safety level determined by the system. |
| Mode Indicator | Graphics and/or name to indicate the currently active mode (MEP, SSEP, Twitch Test, Basic Screw Test, Dynamic Screw Test, Difference Screw Test, Detection, Nerve Retractor). In an alternate embodiment, Graphics and/or name may also be displayed to indicate the instrument in use, such as the dilator, K-wire, retractor blades, screw test instruments, and associated size information, if applicable, of the cannula, with the numeric size. If no instrument is in use, then no indicator is displayed. |
| Stimulation Bar | A graphical stimulation indicator depicting the present stimulation status (ie.. on or off and stimulation current level) |
| Sequence Bar | Shows the last several stimulation results and provides for annotation of results. |
| EMG waveforms | EMG waveforms may be optionally displayed on screen along with the stimulation results. |

Figure 3:
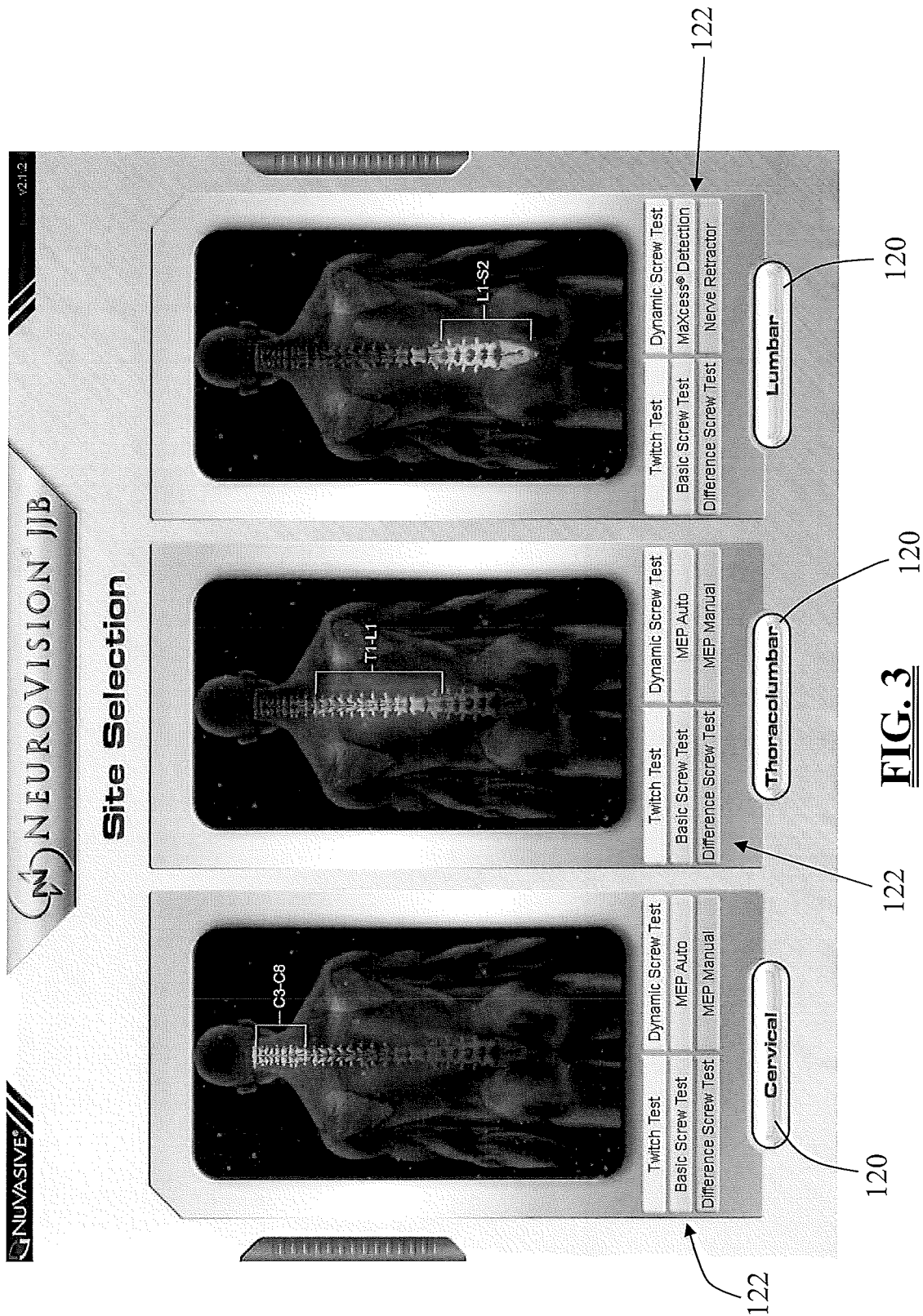
FIG. 3 is an exemplary screen display illustrating a site selection screen for indicating the spinal region to be monitored.

Control of the surgical system 10 is, according to one embodiment, performed by user selection of available options on the GUI display 26, which will now be described (by way of example only) with reference to FIGS. 3-6. FIG. 3 is an exemplary display of a "Site Selection" screen from which a user may initially select the spinal region (i.e. Cervical, Thoracolumbar, or Lumbar) in which the procedure is to be performed by touching one of the site selection tabs 120. EMG electrode placement differs for each spinal region, based on the specific spinal nerves of that region and the associated muscle myotomes. Upon selection of a particular spinal region, each EMG channel is labeled with a myotome according to a preferred EMG configuration for that spinal region.

The Site Selection screen preferably sets forth a list of the modes 122 available for each spinal region. By way of modes are described in greater detail in Int'l Patent App. No. PCT/US02/35047 entitled "System and Methods for Performing Percutaneous Pedicle Integrity Assessments," filed on Oct. 30, 2002, and PCT/US2004/025550, entitled "System and Methods for Performing Dynamic Pedicle Integrity Assessments," filed on Aug. 5, 2004 the entire contents of which are both hereby incorporated by reference as if set forth fully herein. The MaXcess® Detection mode is designed to detect the presence of nerves during the use of the various surgical access instruments of the surgical system 10, including the k-wire 62, dilator 64, cannula 66, retractor assembly 70. This mode is described in greater detail within Int'l Patent App. No PCT/US02/22247, entitled "System and Methods for Determining Nerve Proximity, Direction, and Pathology During Surgery," filed on Jul. 11, 2002, the entire contents of which is hereby incorporated by reference as if set forth fully herein. The Nerve Retractor mode is designed to assess the health or pathology of a nerve before, during, and after retraction of the nerve during a surgical procedure. This mode is described in greater detail within Int'l Patent App. No. PCT/US02/30617, entitled "System and Methods for Performing Surgical Procedures and Assessments," filed on Sep. 25, 2002, the entire contents of which is hereby incorporated by reference as if set forth fully herein. The MEP Auto and MEP Manual modes are designed to test the motor pathway to detect potential damage to the spinal cord by stimulating the motor cortex in the brain and recording the resulting EMG response of various muscles in the upper and lower extremities. These modes will be described in greater detail below.

Figure 4:
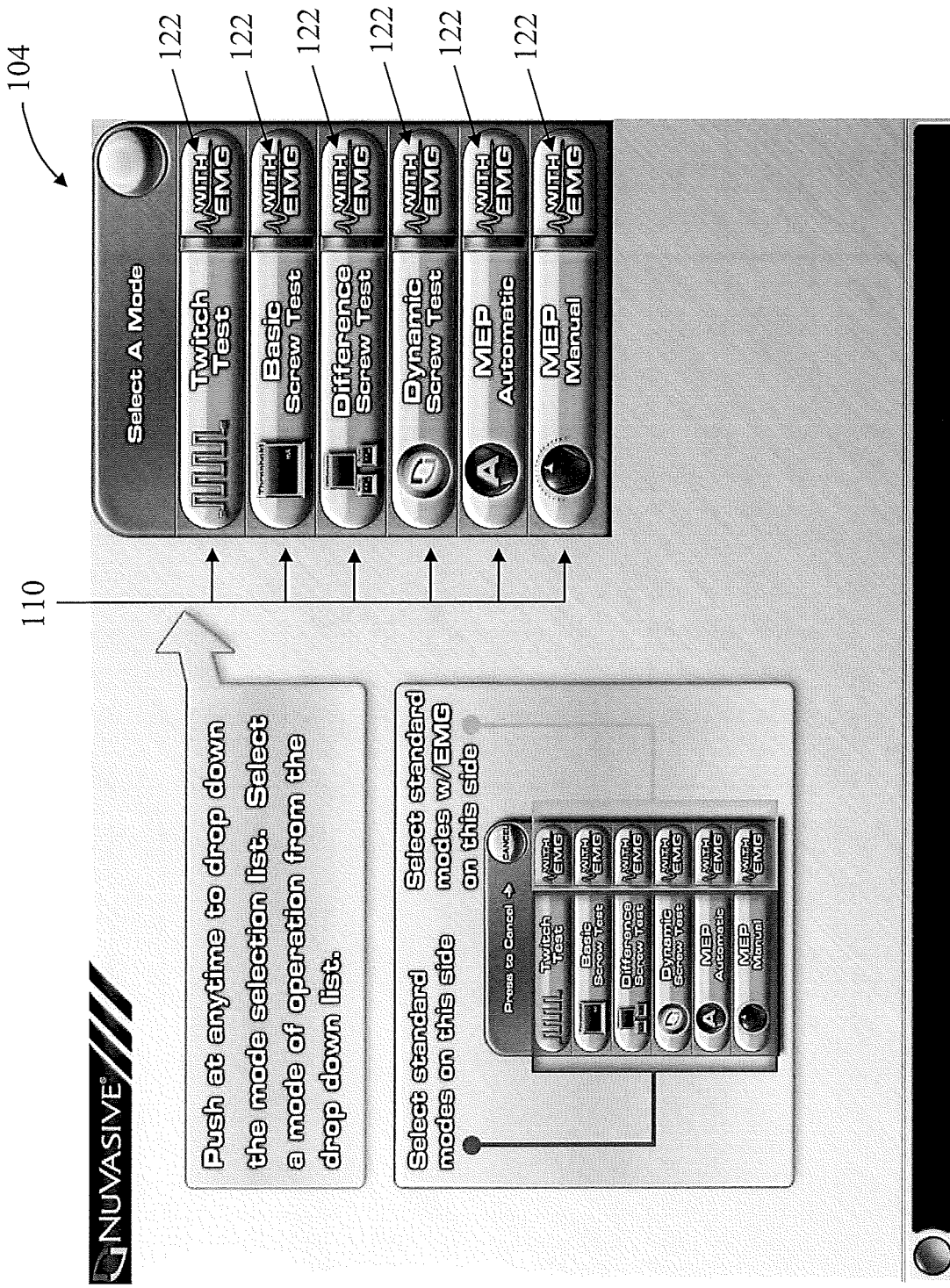
FIG. 4 is an exemplary screen display illustrating a drop down function menu for navigating between different functions of the system 10 during cervical and thoracolumbar procedures.
Figure 5:
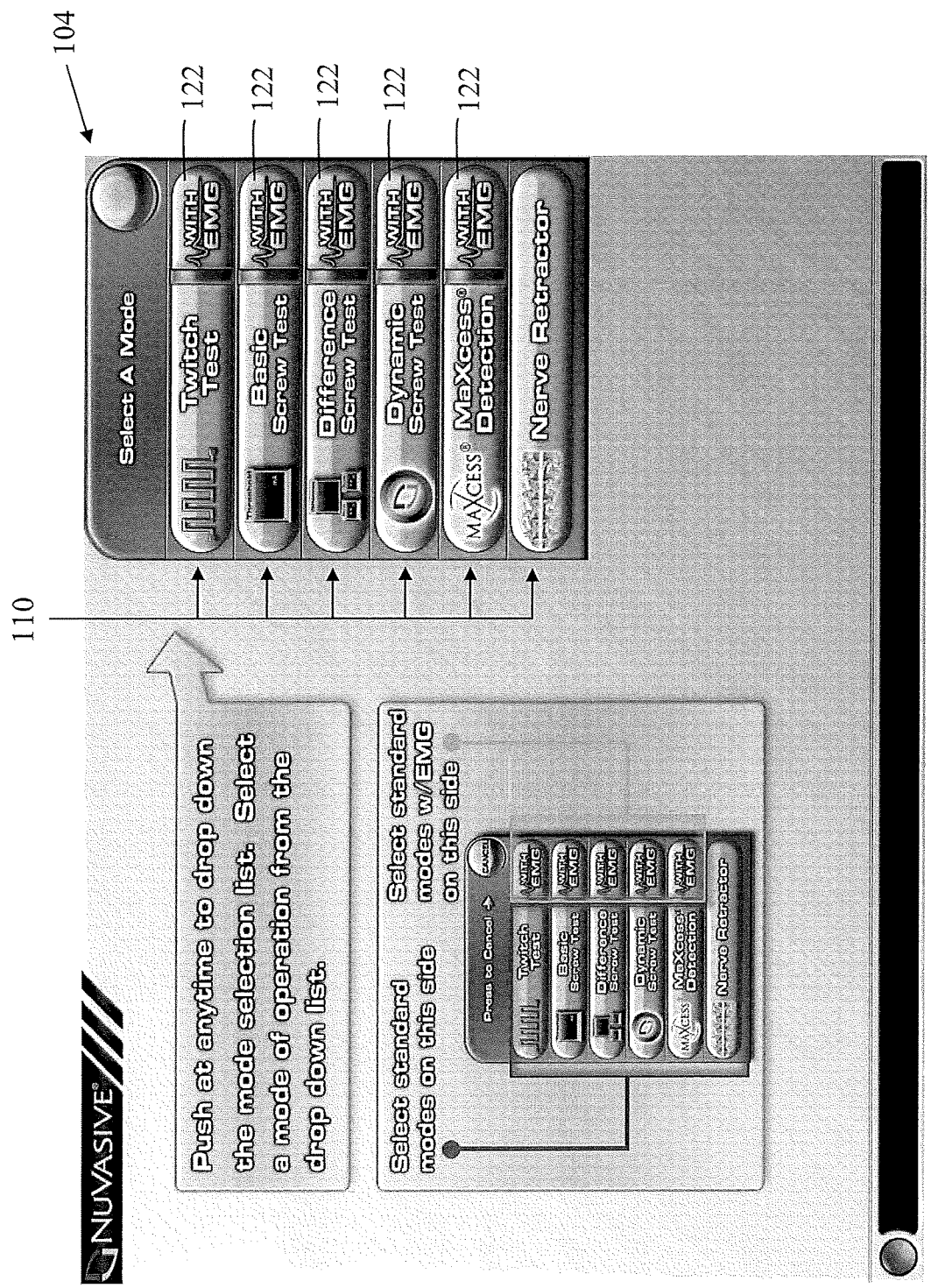
FIG. 5 is an exemplary screen display illustrating another embodiment drop down function menu for navigating between different functions of the system 10 during lumbar procedures.
Figure 6:
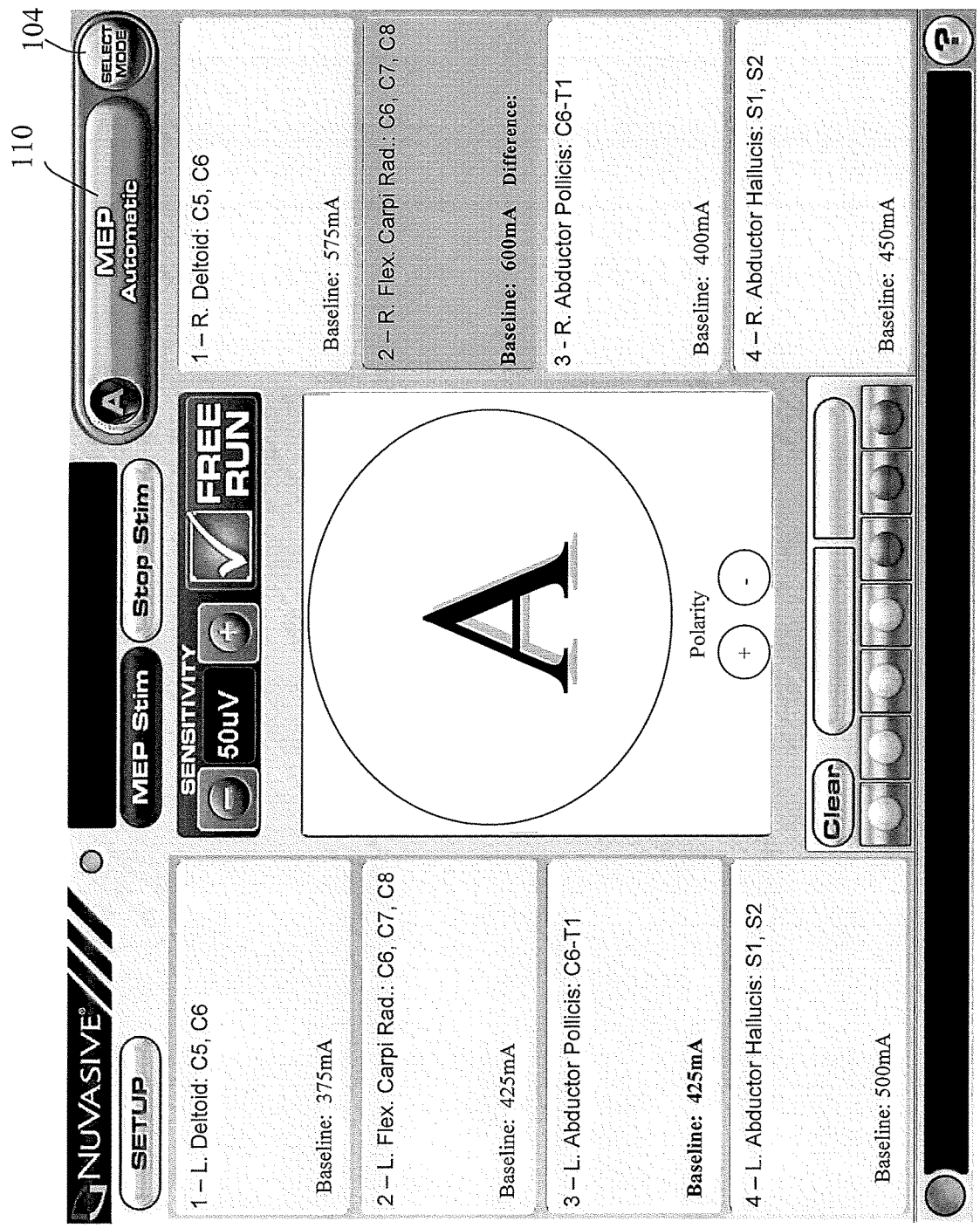
FIG. 6 is an exemplary screen display illustrating a function display screen from which the function menu may be accessed.
Figure 7:
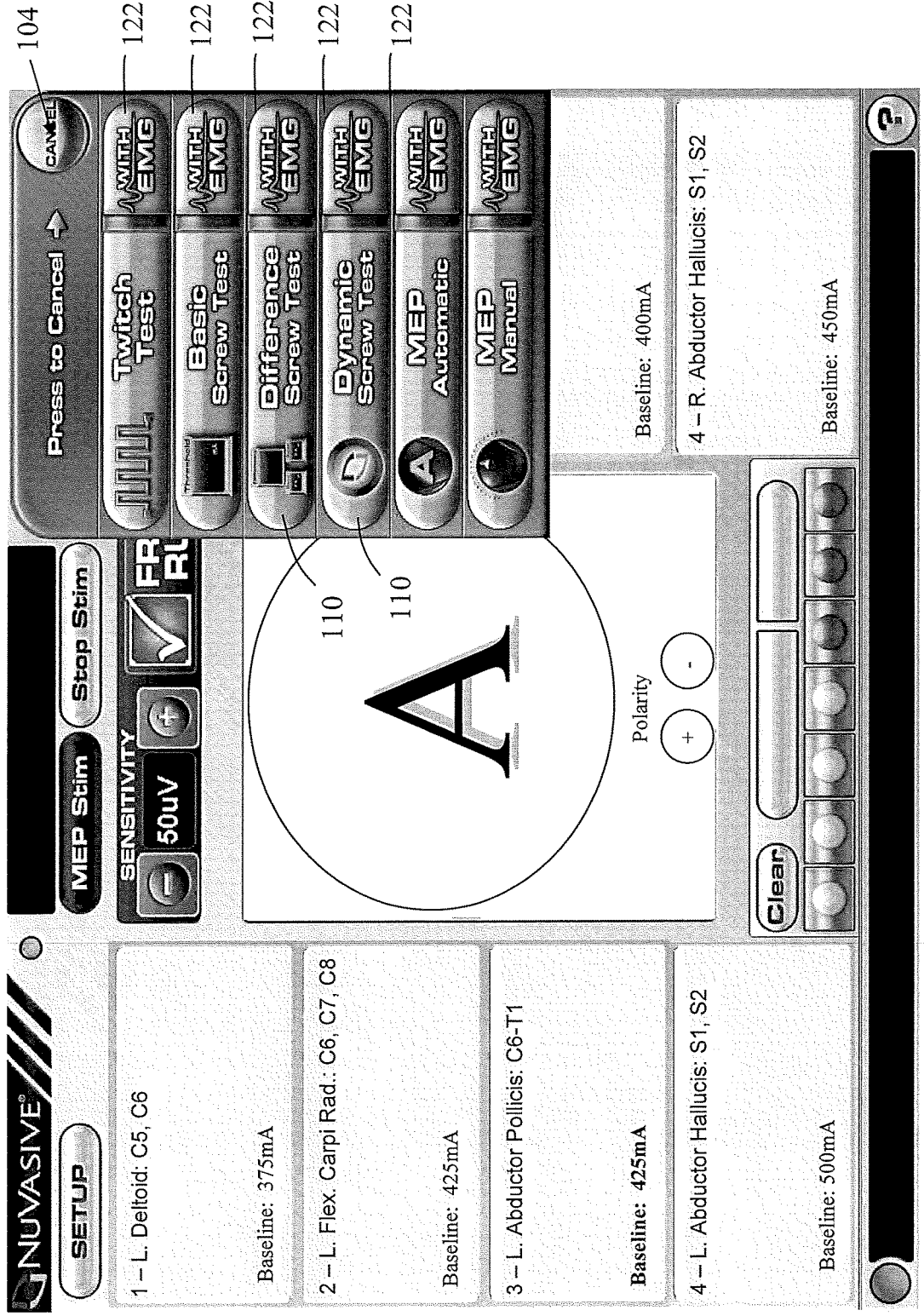
FIG. 7 is exemplary screen display illustrating the function display screen of FIG. 6 in which the function menu has been opened.

Before addressing the MEP and SSEP functionality of the surgical system 10 of the present invention, various general features of the surgical system 10 will be explained. In one embodiment, the surgical system 10 provides the ability to quickly and easily switch or toggle back and forth between different modes during a surgical procedure. Toggling between the various functions of the surgical system 10 may preferably be accomplished by selecting from a drop down mode menu 104, as illustrated in FIGS. 4-5. Upon initial site selection, the mode menu 104 is available on a "menu screen." FIG. 4 represents a menu screen for the cervical and thoracolumbar spinal regions and FIG. 5 represents a menu screen for the lumbar spinal region. The menu screen includes the mode menu 104 and may optionally also include instructions for using and recalling the mode menu 104 at a later time. The mode menu 104 may be recalled directly from the display screen for any given mode, such as the exemplary "MEP Automatic" mode illustrated in FIG. 6-7. Selecting the menu button 118 labeled (by way of example only) "Select Mode" expands and the drop-down mode menu 104 as seen in FIG. 7. Using the menu 104, the surgeon or other qualified user may open any of the functions by selecting the function tab 110 corresponding to the desired function. Also from the menu 104, the user may optionally select to view actual EMG waveforms 116 in addition to the other stimulation results. This is accomplished by selecting an EMG tab (entitled "with EMG") corresponding to the desired function. It should be understood that the drop down menu described above is only a preferred method of navigating between functions and any of a number of different methods may be used. By way of example only, a menu bar containing the different function buttons may be constantly displayed across the top or bottom of the screen.

Figure 8:
FIG. 8 is an exemplary screen display illustrating one embodiment of a general system setup screen.

The surgical system 10 also includes a Setup mode that provides a simple means for selecting and/or changing various options and parameters associated with the surgical system 10 and each the modes. In one embodiment, the display screen for each mode includes a setup tab that allows a user to access and modify the parameters for any or all of the modes. FIG. 8 is an exemplary illustration, set forth by way of example only, of a general system setup screen. From the system set up screen, the user may adjust the system volume, adjust the free-run EMG volume, change the EMG scale, turn the various EMG channels on and off, set the date and time, conduct an impedance test to check the electrical connection between the EMG electrodes and the patient's skin, and shutdown the system 10. The setup options relating to each of the modes (including MEP and SSEP) will be discussed in greater detail below.

Figure 9:
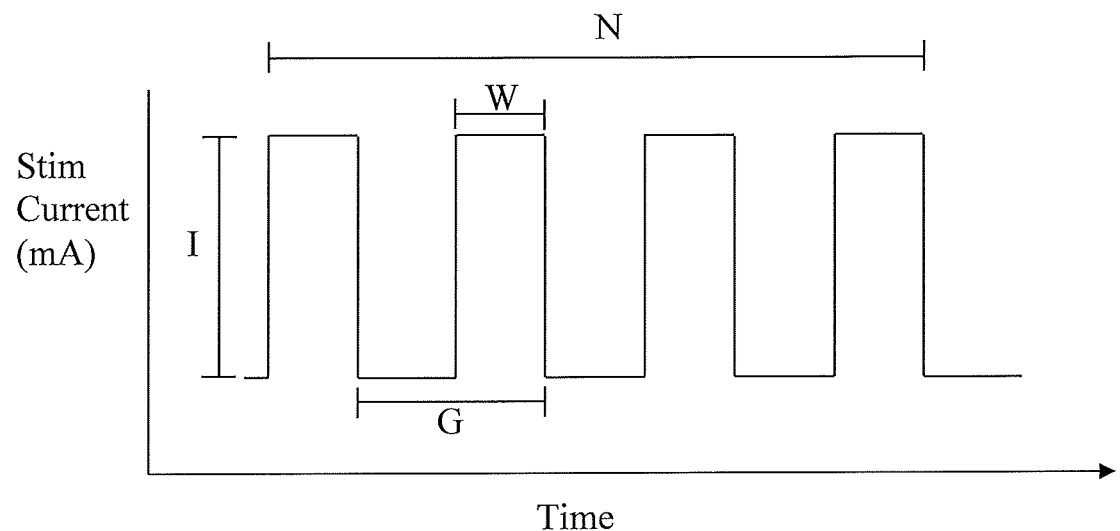
FIG. 9 is a graph illustrating a plot of a stimulation current signal comprising a train of pulses capable of producing a neuromuscular response (EMG) of the type shown in FIG. 10.
Figure 10:
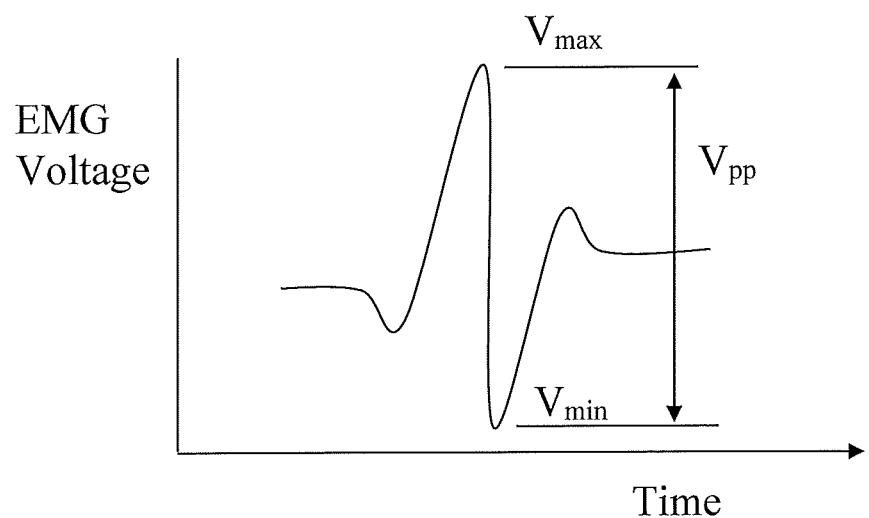
FIG. 10 is a graph illustrating a plot of the neuromuscular response (EMG) of a given myotome over time based on a stimulation signal (such as shown in FIG. 9) applied to the motor cortex and transmitted to a nerve bundle coupled to the given myotome.

The neuromonitoring functionality of the surgical system 10 (except SSEP, which will be described in detail below) is based on assessing the evoked response of the various muscles myotomes monitored by the surgical system 10 in relation to a stimulation signal transmitted by the system 10. This is best shown in FIG. 9-10, wherein FIG. 10 illustrates the resulting EMG of a monitored myotome in response to each pulse of the stimulation signal shown in FIG. 9. The EMG responses provide a quantitative measure of the nerve depolarization caused by the electrical stimulus. In one embodiment, EMG response monitoring is accomplished via 8 pairs EMG electrodes 18 (placed on the skin over the muscle groups to be monitored), a common electrode 20 providing a ground reference to pre-amplifiers in the patient module 14, and an anode electrode 22 providing a return path for the stimulation current. A preferred EMG electrode for use with the system 10 is the dual surface electrode which is shown and described in detail in the commonly owned and co-pending U.S. patent application Ser. No. 11,048,404, entitled "Improved Electrode System and Related Methods," filed on Jan. 31, 2005, which is expressly incorporated by reference into this disclosure as if set forth in its entirety herein. It should be appreciated however, that any of a variety of known electrodes can be employed, including but not limited to surface pad electrodes and needle electrodes. It should also be appreciated that EMG electrode placement depends on a multitude of factors, including for example, the spinal cord level and particular nerves at risk and user preference, among others. Though not essential, electrode placement is preferably undertaken to correspond with the preferred EMG configuration determined during site selection. In one embodiment (set forth by way of example only), the preferred EMG configuration is described for Lumbar in Table 2, Thoracolumbar in Table 3, and Cervical in Table 4 below:

TABLE 2

Lumbar

| Color | Channel | Myotome | Nerve | Spinal Level |
|---|---|---|---|---|
| Red | Right 1 | Right Vastus Medialis | Femoral | L2, L3, L4 |
| Orange | Right 2 | Right Tibialis Anterior | Common Peroneal | L4, L5 |
| Yellow | Right 3 | Right Biceps Femoris | Sciatic | L5, S1, S2 |
| Green | Right 4 | Right Medial Gastroc. | Post Tibial | S1, S2 |
| Blue | Left 1 | Left Vastus Medialis | Femoral | L2, L3, L4 |
| Violet | Left 2 | Left Tibialis Anterior | Common Peroneal | L4, L5 |
| Gray | Left 3 | Left Biceps Femoris | Sciatic | L5, S1, S2 |
| White | Left 4 | Left Medial Gastroc. | Post Tibial | S1, S2 |

TABLE 3

Thoracolumbar

| Color | Channel | Myotome | Nerve | Spinal Level |
|---|---|---|---|---|
| Red | Right 1 | Right Abductor Pollicis Brevis | Median | C6, C7, C8, T1 |
| Orange | Right 2 | Right Vastus Medialis | Femoral | L2, L3, L4 |
| Yellow | Right 3 | Right Tibialis Anterior | Common Peroneal | L4, L5 |
| Green | Right 4 | Right Abductor Hallucis | Tibial | L4, L5, S1 |
| Blue | Left 1 | Left Abductor Pollicis Brevis | Median | C6, C7, C8, T1 |
| Violet | Left 2 | Left Vastus Medialis | Femoral | L2, L3, L4 |
| Gray | Left 3 | Left Tibialis Anterior | Common Peroneal | L4, L5 |
| White | Left 4 | Left Abductor Hallucis | Tibial | L4, L5, S1 |

TABLE 4

| | | Cervical | | |
|---|---|---|---|---|
| Color | Channel | Myotome | Nerve | Spinal Level |
| Red | Right 1 | Right Deltoid | Axilliary | C5, C6 |
| Orange | Right 2 | Right Flexor Carpi Radialis | Median | C6, C7, C8 |
| Yellow | Right 3 | Right Abductor Pollicis Brevis | Median | C6, C7, C8, T1 |
| Green | Right 4 | Right Abductor Hallucis | Tibial | L4, L5, S1 |
| Blue | Left 1 | Left Deltoid | Axillary | C5, C6 |
| Violet | Left 2 | Left Flexor Carpi Radialis | Median | C6, C7, C8 |
| Gray | Left 3 | Left Abductor Pollicis Brevis | Median | C6, C7, C8, T1 |
| White | Left 4 | Left Abductor Hallucis | Tibial | L4, L5, S1 |

In a first broad aspect of the present invention, the surgical system 10 is capable of assessing the health of the spinal cord via MEP monitoring. The surgical system 10 performs the MEP function by transmitting electrical stimulation signals from the MEP stimulator 21 through the motor cortex of the brain. The stimulation signals create action potentials which travel along the spinal cord and into exiting nerve roots, evoking activity from muscles innervated by the nerves. Evoked EMG responses of the muscles are recorded by the system 10 and analyzed in relation to the stimulation signal (discussed below). Resulting data from the analysis is conveyed to the surgeon on the GUI display 26.

MEP stimulation signals are generated in the MEP stimulator 21 and delivered to the motor cortex via stimulation electrodes 23 connected to the MEP stimulator 21. Stimulation electrodes 23 may take the form of needle, corkscrew, or surface pad electrodes, among other known forms. Typically a pair of stimulation electrodes 23, one cathode and one anode, are placed on opposite sides of the skull to transcranially stimulate the motor cortex. In a preferred embodiment, a single MEP stimulation signal includes multiple electrical pulses delivered together as one group or train. Stimulation signals comprising multiple pulses are desirable when stimulating the motor cortex, such as when performing MEP, because a more reliable response can be generated as a result. Each individual pulse of the stimulation signal will cause depolarization (provided the current level is greater than or equal to the stimulation threshold). Each train of pulses (i.e. each individual stimulation signal) is preferably delivered as a series of rectangular monophasic pulses, such as that illustrated, by way of example only, in FIG. 9. The stimulation signal includes a predetermined number of pulses (N) separated by an interpulse gap (G) measured from leading edge to leading edge, each pulse having a pulse width (W) and a current level (I). In one embodiment, the current (I), pulse width (W), and interpulse gap (G) remain constant within a given stimulation signal. By way of example only, MEP stimulator 21 may deliver a stimulation signal comprising four pulses (N=4) having a pulse width of 50 µs (W=50 µs), a current level of 250 mA (I=250 mA), and separated by 2 ms each (G=2 ms). It will be appreciated, however, that these parameters are set forth by way of example only and that any or all of these parameters may be modified without departing from the scope of the present invention.

Figure 11:
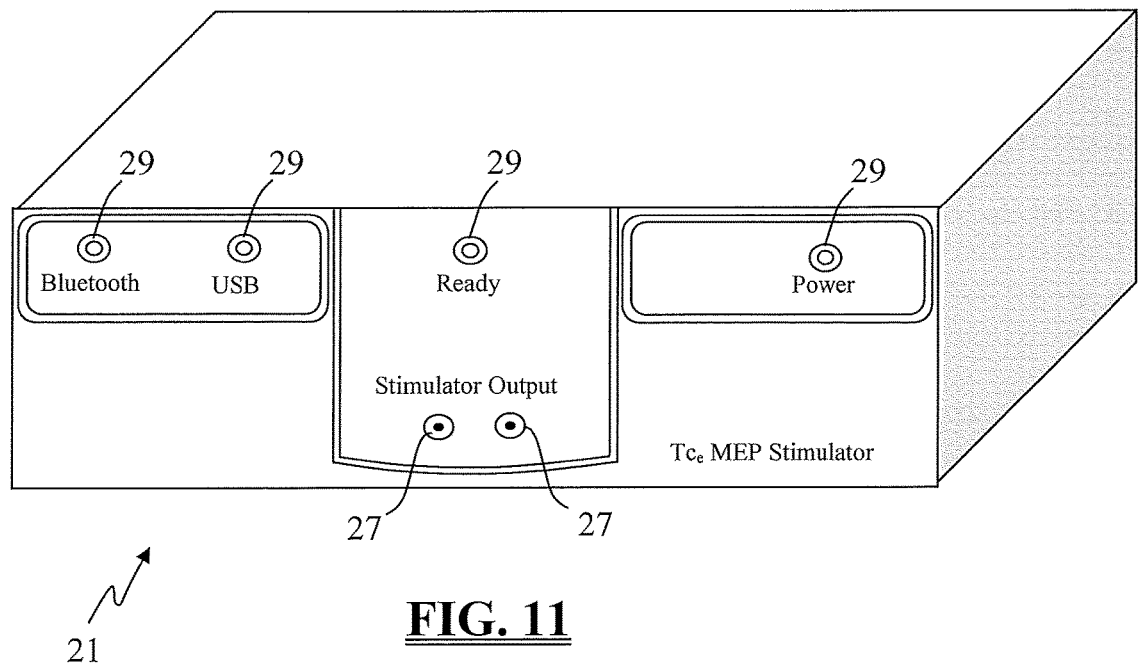
FIG. 11 is a front perspective view of an MEP stimulator capable of delivering high current stimulation signals necessary top elicit MEP responses.
Figure 12:
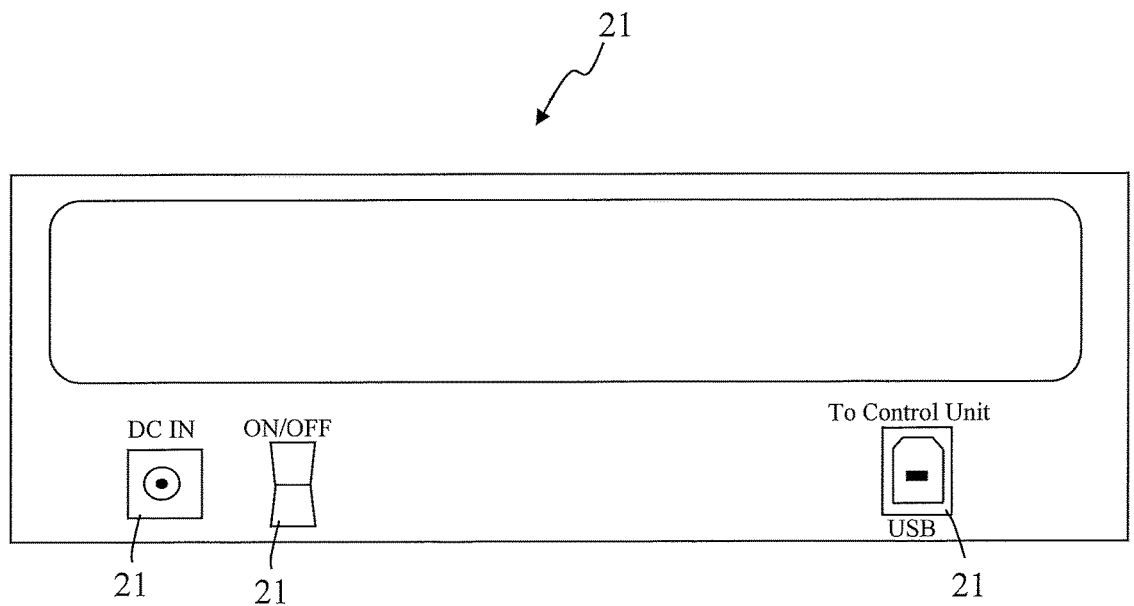
FIG. 12 is a view of the back of the MEP stimulator of FIG. 11.

FIGS. 11 and 12 illustrate front and back views of an example embodiment of MEP stimulator 21, respectively. MEP stimulator 21 includes a high voltage transformer and signal conditioning circuitry (not shown), a communications link to the control unit 12, electrical connections 27 for stimulation electrodes 23, power source connection 35, power switch 33 and LED lights 29 for indicating the type of connection (e.g. wireless Bluetooth connection or USB data cable), whether the power is on, and whether the stimulator 21 is ready to stimulate. In a preferred embodiment, set forth by way of example only, MEP stimulator 21 is current controlled and may deliver stimulation pulses with a current level (I) ranging from 0 mA to 1000 mA. To generate the desired current, stimulator 21 has a voltage output ranging from 0V to 1000V. Stimulation signals generated may include a train of pulses (N) ranging in number from 1 to 8. Pulses may be separated by an interpulse gap (G) ranging from 1 ms to 10 ms and pulse widths (W) may range from 50 µs to 400 µs. MEP stimulator 21 is further capable of delivering either a positive pulse or a negative pulse and may do so automatically or upon manual selection. Additionally, MEP stimulator 21 may have more than one stimulation channel, thus, additional pairs of stimulation electrodes 23 may be arranged on the skull. This may be advantageous in that the effectiveness of a stimulation pulse originating from one position on the skull may vary between different recording sites.

MEP stimulator 21 is communicatively linked to the control unit 12 which commands the stimulator 21 to deliver stimulation signals (according to the predetermined parameters) at the proper time. MEP stimulator 21 may be linked to the control unit 12 with a data cable that connects in any suitable manner or protocol, including but not limited to a USB cable that plugs into a USB port 31 on MEP stimulator 21 and control unit 12. Alternatively, MEP stimulator 21 may be linked to the control unit 12 via wireless technology. By way of example only, this may be accomplished by providing each of the control unit 12 and the MEP stimulator 21 with Bluetooth transceivers, which are commercially available and commonly known in the prior art, allowing the control unit 12 to transmit stimulation commands to the MEP stimulator 21 via a robust radio link. In use, this provides flexibility in positioning the MEP stimulator 21 in relation to the control unit 12, as well as reducing the number of wires and connections required for setup. The MEP stimulator 21 may be positioned outside the sterile area but should be located such that the stimulation electrodes 23, attached to the stimulator 21, may be positioned on the patient's head without tension. By way of example only, MEP stimulator 21 may be placed on the surgical table adjacent to the patient's head. Optionally, the MEP stimulator 21 may be fashioned with a mount or hook (not shown) and hung from the surgical table, an IV pole near the patient's head, or other equipment positioned near the patient.

According to one embodiment, MEP stimulator 21 may be optionally provided with a "bite block" 130 (FIGS. 13-15) to protect the patient's teeth, tongue, and cheeks from potential damage that may be caused by a reflexive clenching of the jaws (bite reflex) which may occur during MEP stimulation. Bite block 130 may be embodied in any of a variety of devices that can be inserted between the upper and lower teeth, absorbing the force of a bite reflex and preventing the tongue and/or cheeks from being bitten. By way of example only, bite block 130 may comprise a generally U shape matching the curvature of the mouth. A bite channel 132 may be provided to encourage proper positioning in the mouth. Preferably, bite block 130 may be disposable and a new bite block provided for each patient. As shown in FIGS. 14-15, one or more electrodes 134 may be incorporated into the bite block 130. By employing electrodes 134 or other moisture sensing features, the system 10 may conduct a safety check and confirm that bite block 130 is properly positioned prior to initiating an MEP stimulation pulse that may result in a bite reflex.

In the embodiment of FIG. 14, two electrodes 134 (one positive (anode) and one negative (cathode)) may be positioned near the distal ends of bite block 130 such that a gap, indicated by line X, exists between the electrodes 134. Attachable cables 136 may communicatively link the electrodes 134 to patient module 14. Alternatively, the electrodes 134 may be connected to MEP stimulator 21 via attachable cables 136. The surgical system 10 confirms bite block 130 is in position by applying a small electrical current, via patient module 14 or MEP stimulator 21, to the cathode electrode and measuring the impedance between the cathode and anode. Positioning bite block 130 in the mouth moistens electrodes 134 which results in a decrease in the impedance value. Conversely, if the bite block 130 is not positioned in the mouth, the electrodes 134 may not be moistened and the impedance value will be substantially higher.

In the embodiment of FIG. 15, one electrode 134 may be incorporated into bite block 130 and connected to the MEP stimulator via attachable cable 136. Electrode 134 may be employed in conjunction with stimulation electrode 23 to conduct the safety check and confirm bite block 130 is in position prior to initiating MEP stimulation. The system 10 applies a small electrical current to the stimulation electrode 23 located on the head and the impedance between the stimulation electrode 23 and the bite block electrode 134 is determined. If the impedance value is not within a predetermined safe range, it may be an indication that the bite block 130 is not positioned properly thus decreasing its effectiveness. The bite block 130 may be repositioned and tested again until the impedance test indicates proper positioning.

In a still further embodiment, electrode 134 of bite block 130 may comprise one of MEP stimulation electrodes 23. Electrode 134 is connected, via an attachable cable 136, to MEP stimulator 21 on the same stimulation channel as the corresponding stimulation electrode 23. In this manner, transcranial stimulation of the motor cortex is achieved by sending an MEP stimulation pulse from an electrode on the top of the head to an electrode located in the mouth, as opposed to sending the stimulation signal from one side of the head to the other. In addition to providing an alternate path for the stimulation pulse, utilizing the bite block 130 as a part of the stimulation circuit ensures that the protective bite block 130 is in position prior to MEP stimulation. Additionally, the impedance tests described above may be implemented through this embodiment.

Although bite block 130 has been described above with reference to the surgical system 10, it will be appreciated as within the scope of the invention to use bite block 130 in conjunction with any device or system used for MEP stimulation. It will be further appreciated as not departing from the scope of the invention that bite block 130 may be implemented as an independent system utilizing its own electrical source or the electrical source of any system it may be used in conjunction with, for any of a variety of situations where confirming placement of a bite block may be beneficial.

Figure 16:
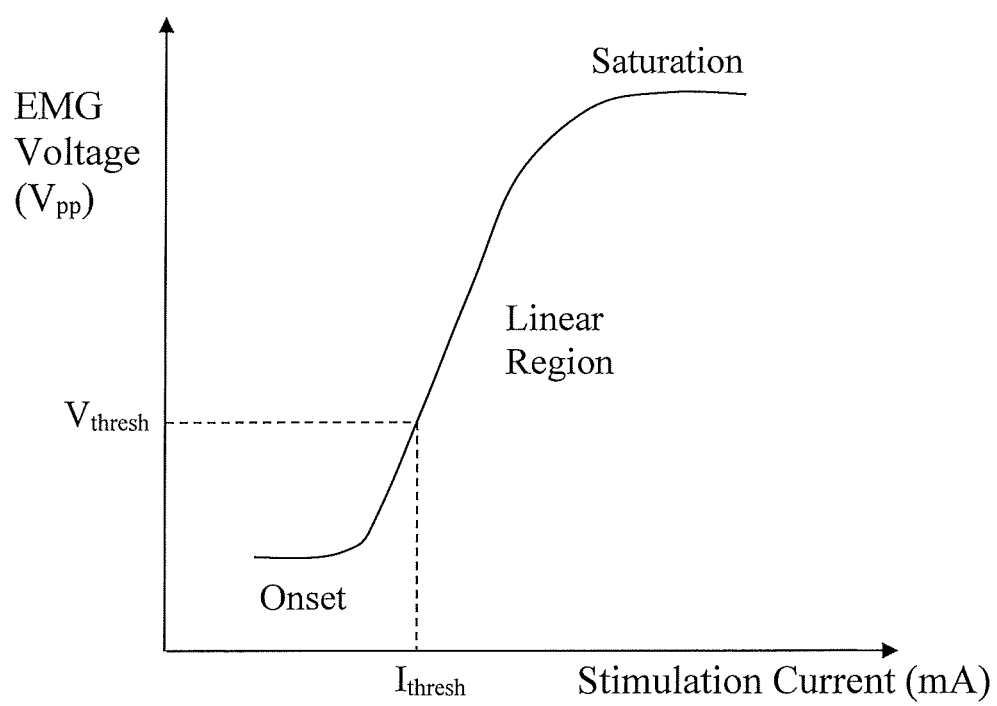
FIG. 16 is a graph illustrating a plot of EMG response peak-to-peak voltage (Vpp) for each given stimulation current level ($I_{Stim}$) forming a stimulation current pulse according to the present invention (otherwise known as a "recruitment curve")

A basic premise underlying the methods employed by the system 10 for MEP monitoring (as well as the other nerve monitoring functions conducted by system 10) is that neurons and nerves have characteristic threshold current levels ($I_{Thresh}$) at which they will depolarize, resulting in detectable muscle activity. Below this threshold current, stimulation signals will not evoke a significant EMG response. Each EMG response can be characterized by a peak-to-peak voltage of $V_{pp}=V_{max}-V_{min}$, shown in FIG. 10. Once the stimulation threshold ($I_{Thresh}$) is reached, the evoked response is reproducible and increases with increasing stimulation until saturation is reached as shown in FIG. 16. This is known as a "recruitment curve." In one embodiment, a significant EMG response is defined as having a $V_{pp}$ of approximately 100 uV. The lowest stimulation signal current that evokes this threshold voltage ($V_{Thresh}$) is called $I_{Thresh}$. $I_{thresh}$ increases as the degree of electrical communication between a stimulation signal and a nerve decreases and conversely, $I_{thresh}$ decreases as the electrical communication increases between the nerve and stimulation pulse. Thus monitoring $I_{thresh}$ during MEP can provide the surgeon with useful information about the health of the spinal cord. For example, if $I_{thresh}$ is too high or increases from a previous measurement, it may indicate a problem in the spinal cord inhibiting transmission (communication) of the stimulation signal to the nerve. $I_{thresh}$ can be conveyed as a simple numerical value, thereby providing the surgeon with simple, comprehensible data from the MEP test, without the need for separate analysis by other highly trained personnel. Calculating $I_{thresh}$ also provides valuable information for other nerve monitoring functions, including, but not necessarily limited to, pedicle screw testing nerve proximity monitoring, and nerve pathology monitoring. Armed with the useful information conveyed by $I_{thresh}$, the surgeon may detect a problem or potential problem early and then act to avoid and/or mitigate the problem.

To obtain $I_{thresh}$ and take advantage of the useful information it provides, the system 10 identifies and measures the peak-to-peak voltage ($V_{pp}$) of each EMG response corresponding to a given stimulation current ($I_{Stim}$). Identifying the true $V_{pp}$ of a response may be complicated by the existence of stimulation and/or noise artifacts which may create an erroneous $V_{pp}$ measurement. To overcome this challenge, the surgical system 10 of the present invention may employ any number of suitable artifact rejection techniques such as those shown and described in full in the above referenced co-pending and commonly assigned PCT App. Ser. No. PCT/US2004/025550, entitled "System and Methods for Performing Dynamic Pedicle Integrity Assessments," filed on Aug. 5, 2004. Upon measuring $V_{pp}$ for each EMG response, the $V_{pp}$ information is analyzed relative to the corresponding stimulation current ($I_{stim}$) in order to identify the minimum stimulation current ($I_{Thresh}$) capable of resulting in a predetermined $V_{pp}$ EMG response. According to the present invention, the determination of $I_{Thresh}$ may be accomplished via any of a variety of suitable algorithms or techniques.

FIGS. 17A-17D illustrates, by way of example only, the basic principles of a threshold hunting algorithm of the present invention used to quickly find $I_{thresh}$ during MEP monitoring. $I_{thresh}$ is, once again, the minimum stimulation current ($I_{stim}$) that results in an EMG response with a $V_{pp}$ greater than a known threshold voltage, $V_{thresh}$. The method for finding $I_{thresh}$ for MEP according to the present invention utilizes a bracketing method and a bisection method. The bracketing method quickly finds a range (bracket) of stimulation currents that must contain $I_{thresh}$ and the bisection method narrows the bracket until $I_{thresh}$ is known within a specified accuracy. If the stimulation current threshold, $I_{thresh}$, of a channel exceeds a maximum stimulation current, that threshold is considered out of range.

Figure 17A:
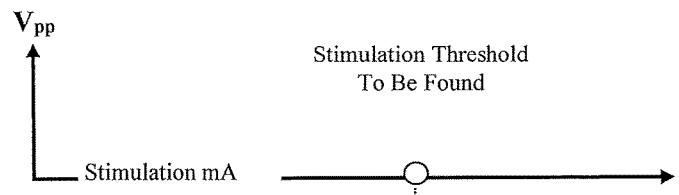
FIGS. 17A-17D are graphs illustrating the fundamental steps of a rapid current threshold-hunting algorithm according to one embodiment of the present invention.
Figure 17B:
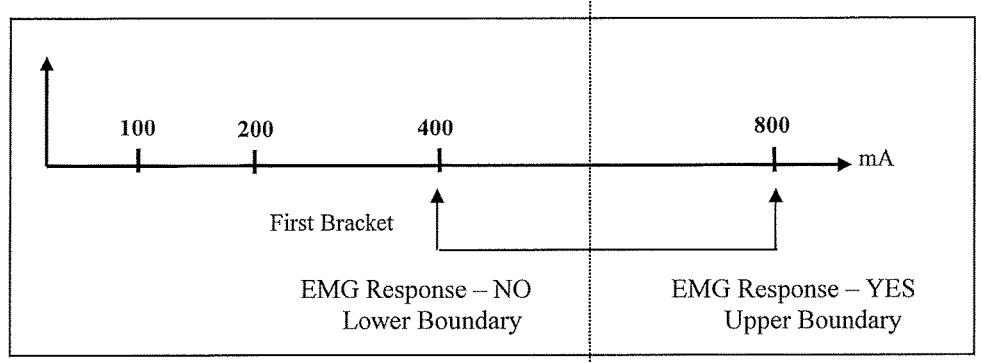

FIG. 17B illustrates the bracketing feature of the MEP threshold hunting algorithm of the present invention. Stimulation begins at a minimum stimulation current, such as (by way of example only) 100 mA. The level of each subsequent stimulation is doubled from the preceding stimulation level until a stimulation current recruits (i.e. results in an EMG response with a $V_{pp}$ greater or equal to $V_{thresh}$). The first stimulation current to recruit (800 mA in FIG. 17B), together with the last stimulation current to have not recruited (400 mA in FIG. 17B), forms the initial bracket.

Figure 17C:
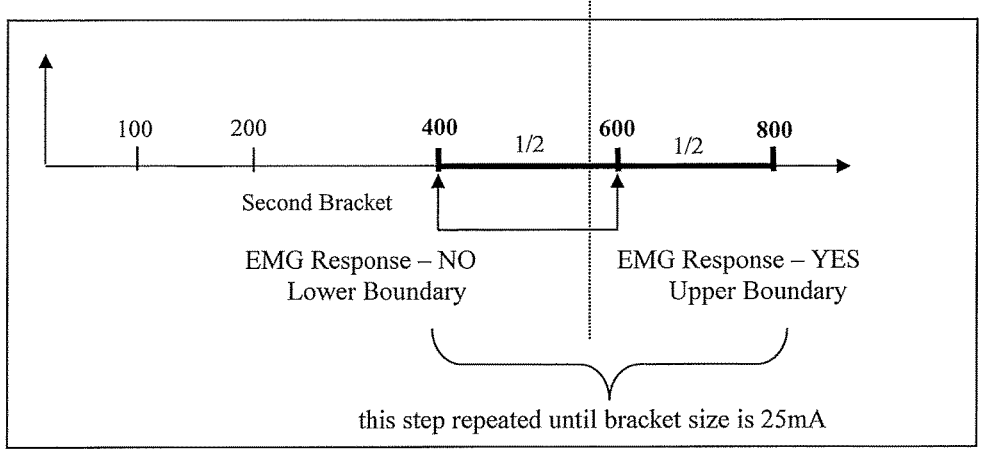
Figure 17D:
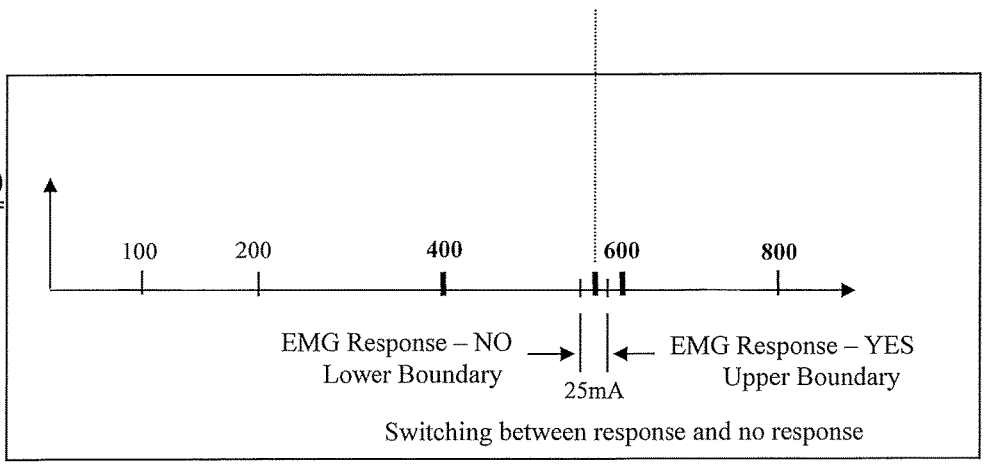

FIGS. 17C-17D illustrate the bisection feature of the MEP threshold hunting algorithm of the present invention. After the threshold current $I_{thresh}$ has been bracketed (FIG. 17B), the initial bracket is successively reduced via bisection to a predetermined width, such as (by way of example only) 25 mA. This is accomplished by applying a first bisection stimulation current that bisects (i.e. forms the midpoint of) the initial bracket (600 mA in FIG. 17C). If this first bisection stimulation current recruits, the bracket is reduced to the lower half of the initial bracket (e.g. 400 mA and 600 mA in FIG. 17C). If this first bisection stimulation current does not recruit, the bracket is reduced to the upper half of the initial bracket (e.g. 600 mA and 800 mA in FIG. 17C). This process is continued for each successive bracket until $I_{thresh}$ is bracketed by stimulation currents separated by the predetermined width (which, in this case, is 25 mA). In this example shown, this would be accomplished by applying a second bisection stimulation current (forming the midpoint of the second bracket, or 500 mA in this example). Because this second bisection stimulation current is below $I_{thresh}$, it will not recruit. As such, the second bracket will be reduced to the upper half thereof (500 mA to 600 mA), forming a third bracket. A third bisection stimulation current forming the mid-point of the third bracket (550 mA in this case) will then be applied. Because this third bisection stimulation current is below $I_{thresh}$, it will not thresh, recruit. As such, the third bracket will be reduced to the upper half thereof (550 mA to 600 mA), forming a fourth bracket. A fourth bisection stimulation current forming the mid-point of the fourth bracket (575 mA in this case) will then be applied. Because the fourth bisection stimulation current is above $I_{thresh}$, it will recruit. The final bracket is therefore thresh, between 550 mA and 575 mA. Due to the "response" or recruitment at 550 mA and "no response" or lack of recruitment at 575 mA, it can be inferred that $I_{thresh}$ is within this range. In one embodiment, the midpoint of this final bracket may be defined as $I_{thresh}$, however, any any value falling within the final bracket may be selected as $I_{thresh}$ without departing from the scope of the present invention. Depending on the active mode, the algorithm may stop after finding $I_{thresh}$ for the first responding channel (i.e. the channel with the lowest $I_{thresh}$) or the bracketing and bisection steps may be repeated for each channel to determine $I_{thresh}$ for each channel.

For some functions, such as (by way of example) MEP monitoring, it may be desirable to obtain $I_{thresh}$ for each active channel each time the MEP function is performed. This is particularly advantageous when assessing changes in $I_{thresh}$ over time as a means to detect potential problems (as opposed to detecting an $I_{thresh}$ below a predetermined level determined to be safe, such as in the Screw Test modes). While $I_{thresh}$ can be found for each active channel using the algorithm as described above, it requires a potentially large number of stimulations, each of which is associated with a specific time delay, which can add significantly to the response time. Done repeatedly, it could also add significantly to the overall time required to complete the surgical procedure, which may present added risk to the patient and added costs. To overcome this drawback, a preferred embodiment of the surgical system 10 boasts a multi-channel MEP threshold hunting algorithm so as to quickly determine $I_{thresh}$ for each channel while minimizing the number of stimulations and thus reduce the time required to perform such determinations.

The multi-channel MEP threshold hunting algorithm reduces the number stimulations required to complete the bracketing and bisection steps when $I_{thresh}$ is being found for multiple channels. The multi-channel algorithm does so by omitting stimulations for which the result is predictable from the data already acquired. When a stimulation signal is omitted, the algorithm proceeds as if the stimulation had taken place. However, instead of reporting an actual recruitment result, the reported result is inferred from previous data. This permits the algorithm to proceed to the next step immediately, without the time delay associated with a stimulation signal.

Regardless of what channel is being processed for $I_{thresh}$, each stimulation signal elicits a response from all active channels. That is to say, every channel either recruits or does not recruit in response to a stimulation signal (again, a channel is said to have recruited if a stimulation signal evokes an EMG response deemed to be significant on that channel, such as $V_{pp}$ of approximately 100 uV). These recruitment results are recorded and saved for each channel. Later, when a different channel is processed for $I_{thresh}$, the saved data can be accessed and, based on that data, the algorithm may omit a stimulation signal and infer whether or not the channel would recruit at the given stimulation current.

There are two reasons the algorithm may omit a stimulation signal and report previous recruitment results. A stimulation signal may be omitted if the selected stimulation current would be a repeat of a previous stimulation. By way of example only, if a stimulation current of 100 mA was applied to determine $I_{thresh}$ for one channel, and a stimulation at 100 mA is later required to determine $I_{thresh}$ for another channel, the algorithm may omit the stimulation and report the previous results. If the specific stimulation current required has not previously been used, a stimulation signal may still be omitted if the results are already clear from the previous data. By way of example only, if a stimulation current of 200 mA was applied to determine $I_{thresh}$ for a previous channel and the present channel did not recruit, when a stimulation at 100 mA is later required to determine $I_{thresh}$ for the present channel, the algorithm may infer from the previous stimulation that the present channel will not recruit at 100 mA because it did not recruit at 200 mA. The algorithm may therefore omit the stimulation and report the previous result.

Figure 18:
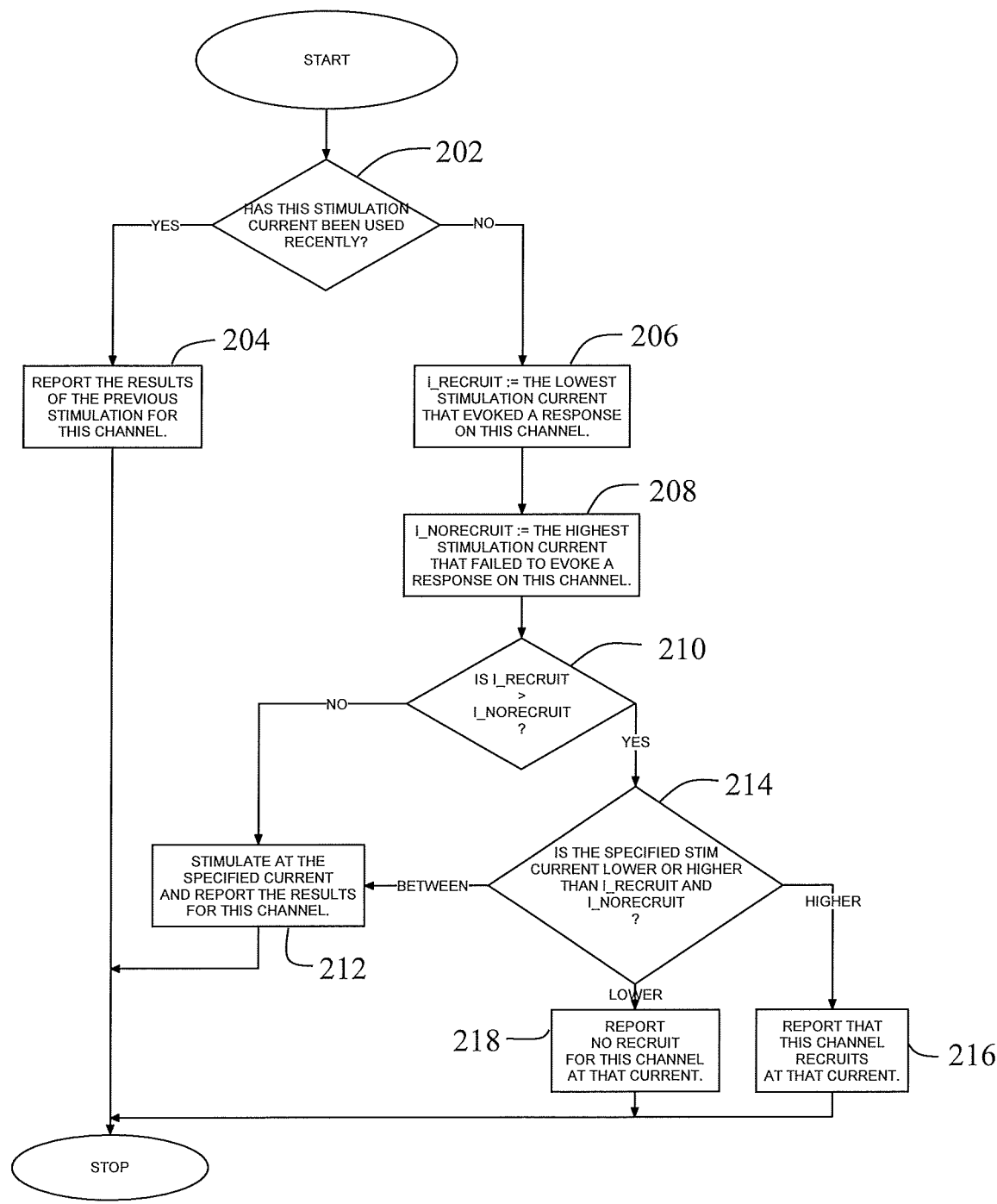
FIG. 18 is a flowchart illustrating the method by which a multi-channel hunting algorithm determines whether to perform or omit a stimulation.

FIG. 18 illustrates (in flowchart form) a method by which the multi-channel MEP threshold hunting algorithm determines whether to stimulate, or not stimulate and simply report previous results. The algorithm first determines if the selected stimulation current has already been used (step 202). If the stimulation current has been used, the stimulation is omitted and the results of the previous stimulation are reported for the present channel (step 204). If the stimulation current has not been used, the algorithm determines $I_{recruit}$ (step 206) and $I_{norecruit}$ (step 208) for the present channel. $I_{recruit}$ is the lowest stimulation current that has recruited on the present channel. $I_{norecruit}$ is the highest stimulation current that has failed to recruit on the present channel. The algorithm next determines whether $I_{recruit}$ is greater than $I_{norecruit}$ (step 210). An $I_{recruit}$ that is not greater than $I_{norecruit}$ is an indication that changes have occurred to $I_{thresh}$ on that channel. Thus, previous results may not be reflective of the present threshold state and the algorithm will not use them to infer the response to a given stimulation current. The algorithm will stimulate at the selected current and report the results for the present channel (step 212). If $I_{recruit}$ is greater than $I_{norecruit}$, the algorithm determines whether the selected stimulation current is higher than $I_{recruit}$, lower than $I_{norecruit}$, or between $I_{recruit}$ and $I_{norecruit}$ (step 214). If the selected stimulation current is higher than $I_{recruit}$, the algorithm omits the stimulation and reports that the present channel recruits at the specified current (step 216). If the selected stimulation current is lower than $I_{norecruit}$, the algorithm infers that the present channel will not recruit at the selected current and reports that result (step 218). If the selected stimulation current falls between $I_{recruit}$ and $I_{norecruit}$, the result of the stimulation cannot be inferred and the algorithm stimulates at the selected current and reports the results for the present channel (step 212). This method may be repeated until $I_{thresh}$ has been determined for every active channel.

Figure 19A:
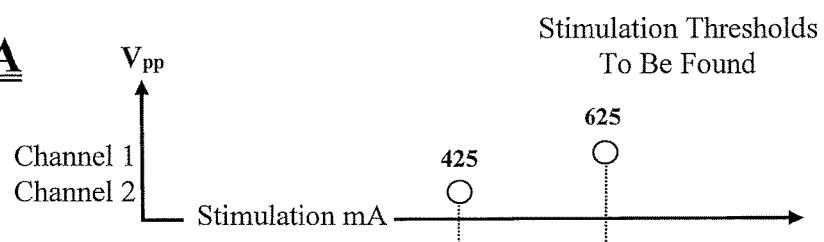
FIGS. 19A-19C are graphs illustrating use of the threshold hunting algorithm of FIG. 17 and further omitting stimulations when the likely result is already clear from previous data.
Figure 19B:
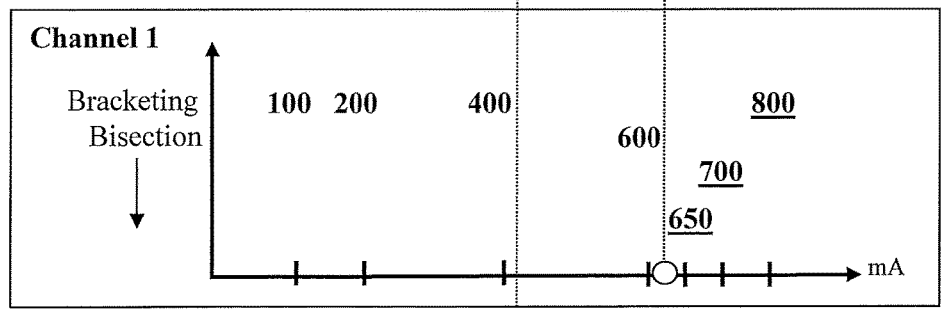
Figure 19C:
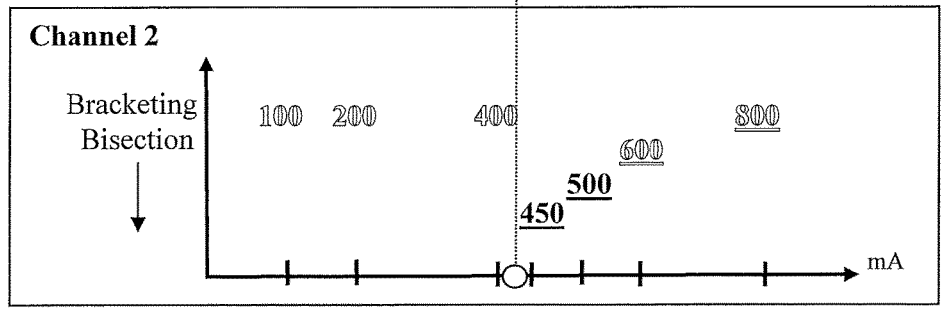

In the interest of clarity, FIGS. 19A-19C demonstrate use of the multi-channel MEP threshold hunting algorithm to determine $I_{thresh}$ on only two channels. It should be appreciated, however, that the multi-channel algorithm is not limited to finding $I_{thresh}$ for two channels, but rather it may be used to find $I_{thresh}$ for any number of channels, such as (for example) eight channels according to a preferred embodiment of the surgical system 10. With reference to FIG. 19A, channel 1 has an $I_{thresh}$ to be found of 625 mA and channel 2 has an $I_{thresh}$ to be found of 425 mA. $I_{thresh}$ for channel 1 is found first, using the bracketing and bisection methods discussed above, as illustrated in FIG. 17B. Bracketing begins at the minimum stimulation current (for the purposes of example only) of 100 mA. As this is the first channel processed and no previous recruitment results exist, no stimulations are omitted. The stimulation current is doubled with each successive stimulation until a significant EMG response is evoked at 800 mA. The initial bracket of 400 mA-800 mA is bisected, using the bisection method described above, until the stimulation threshold, $I_{thresh}$, is contained within a final bracket separated by the selected width or resolution (again 25 mA). In this example, the final bracket is 600 mA-625 mA. $I_{thresh}$ may be defined as any point within the final bracket or as the midpoint of the final bracket (612.5 mA in this case). In either event, $I_{thresh}$ is selected and reported as $I_{thresh}$ for channel 1.

Once $I_{thresh}$ is found for channel 1, the algorithm turns to channel 2, as illustrated in FIG. 19C. The algorithm begins to process channel 2 by determining the initial bracket, which is again 400 mA-800 mA. All the stimulation currents required in the bracketing state were used in determining $I_{thresh}$ for channel 1. The algorithm refers back to the saved data to determine how channel 1 responded to the previous stimulations. From the saved data, the algorithm may infer that channel 2 will not recruit at stimulation currents of 100, 200, and 400 mA, and will recruit at 800 mA. These stimulations are omitted and the inferred results are displayed. The first bisection stimulation current selected in the bisection process (600 mA in this case), was previously used and, as such, the algorithm may omit the stimulation and report that channel 2 recruits at that stimulation current. The next bisection stimulation current selected (500 mA in this case) has not been previously used and, as such, the algorithm must determine whether the result of a stimulation at 500 mA may still be inferred. In the example shown, $I_{recruit}$ and $I_{norecruit}$ are determined to be 600 mA and 400 mA, respectively. Because 500 mA falls in between $I_{recruit}$ and $I_{norecruit}$, the algorithm may not infer the result from the previous data and, as such, the stimulation may not be omitted. The algorithm then stimulates at 500 mA and reports that the channel recruits. The bracket is reduced to the lower half (making 450 mA the next bisection stimulation current). A stimulation current of 450 mA has not previously been used and, as such, the algorithm again determines $I_{recruit}$ and $I_{norecruit}$ (500 mA and 400 mA in this case). The selected stimulation current (450 mA) falls in between $I_{recruit}$ an $I_{norecruit}$ and, as such, the algorithm stimulates at 450 mA and reports the results. The bracket now stands at its final width of 625 mA (for the purposes of example only). $I_{thresh}$ may be defined as any point within the final bracket or as the midpoint of the final bracket (412.5 mA in this case). In either event, $I_{thresh}$ is selected and reported as $I_{thresh}$ for channel 2.

Although the multi-channel MEP threshold hunting algorithm is described above processing channels in numerical order, it will be understood that the actual order in which channels are processed is immaterial. The channel processing order may be biased to yield the highest or lowest threshold first (discussed below) or an arbitrary processing order may be used. Furthermore, it will be understood that it is not necessary to complete the algorithm for one channel before beginning to process the next channel, provided that the intermediate state of the algorithm is retained for each channel. Channels are still processed one at a time. However, the algorithm may cycle between one or more channels, processing as few as one stimulation current for that channel before moving on to the next channel. By way of example only, the algorithm may stimulate at 100 mA while processing a first channel for $I_{thresh}$. Before stimulating at 200 mA (the next stimulation current in the bracketing phase), the algorithm may cycle to any other channel and process it for the 100 mA stimulation current (omitting the stimulation if applicable). Any or all of the channels may be processed this way before returning to the first channel to apply the next stimulation. Likewise, the algorithm need not return to the first channel to stimulate at 200 mA, but instead may select a different channel to process first at the 200 mA level. In this manner, the algorithm may advance all channels essentially together and bias the order to find the lower threshold channels first or the higher threshold channels first. By way of example only, the algorithm may stimulate at one current level and process each channel in turn at that level before advancing to the next stimulation current level. The algorithm may continue in this pattern until the channel with the lowest $I_{thresh}$ is bracketed. The algorithm $I_{thresh}$ is may then process that channel exclusively until $I_{thresh}$ is determined, and then return to processing the other channels one stimulation current level at a time until the channel with the next lowest $I_{thresh}$ bracketed. This process may be repeated until $I_{thresh}$ is determined for each channel in order of lowest to highest $I_{thresh}$. If $I_{thresh}$ for more than one channel falls within the same bracket, the bracket may be bisected, processing each channel within that bracket in turn until it becomes clear which one has the lowest $I_{thresh}$. If it becomes more advantageous to determine the highest $I_{thresh}$ first, the algorithm may continue in the bracketing state until the bracket is found for every channel and then bisect each channel in descending order.

Figure 20:
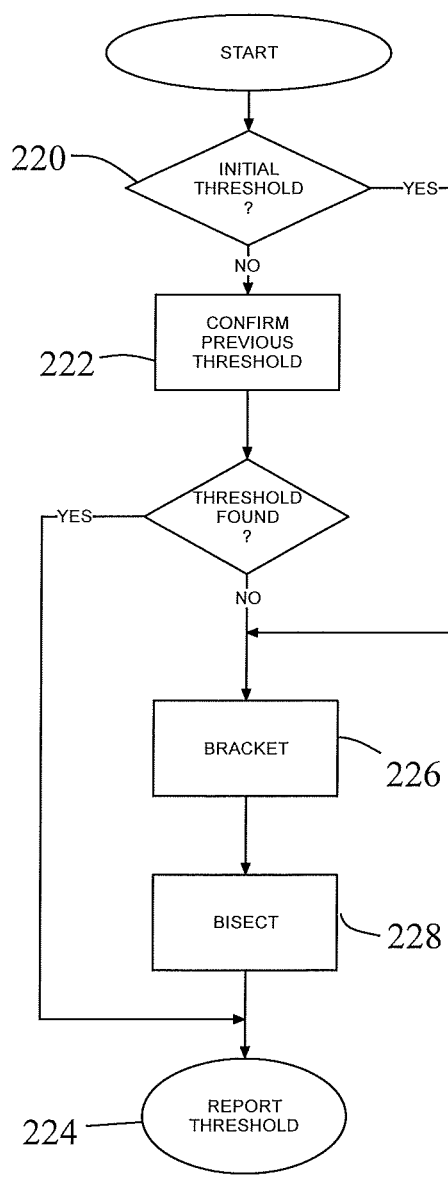
FIG. 20 is a flowchart illustrating the sequence employed by the algorithm to determine and monitor $I_{thresh}$.

FIG. 20 illustrates a further feature of the MEP threshold hunting algorithm of the present invention, which advantageously provides the ability to further reduce the number of stimulations required to find $I_{thresh}$ when an $I_{thresh}$ value has previously been determined for a specific channel. In the event that a previous $I_{thresh}$ determination exists for a specific channel, the algorithm may begin by merely confirming the previous $I_{thresh}$ rather than beginning anew with the bracketing and bisection methods. The algorithm first determines whether it is conducting the initial threshold determination for the channel or whether there is a previous $I_{thresh}$ determination (step 220). If it is not the initial determination, the algorithm confirms the previous determination (step 222) as described below. If the previous threshold is confirmed, the algorithm reports that value as the present $I_{thresh}$ (step 224). If it is the initial $I_{thresh}$ determination, or if the previous threshold cannot be confirmed, then the algorithm performs the bracketing function (step 226) and bisection function (step 228) to determine $I_{thresh}$ and then reports the value (step 224).

Figure 21:
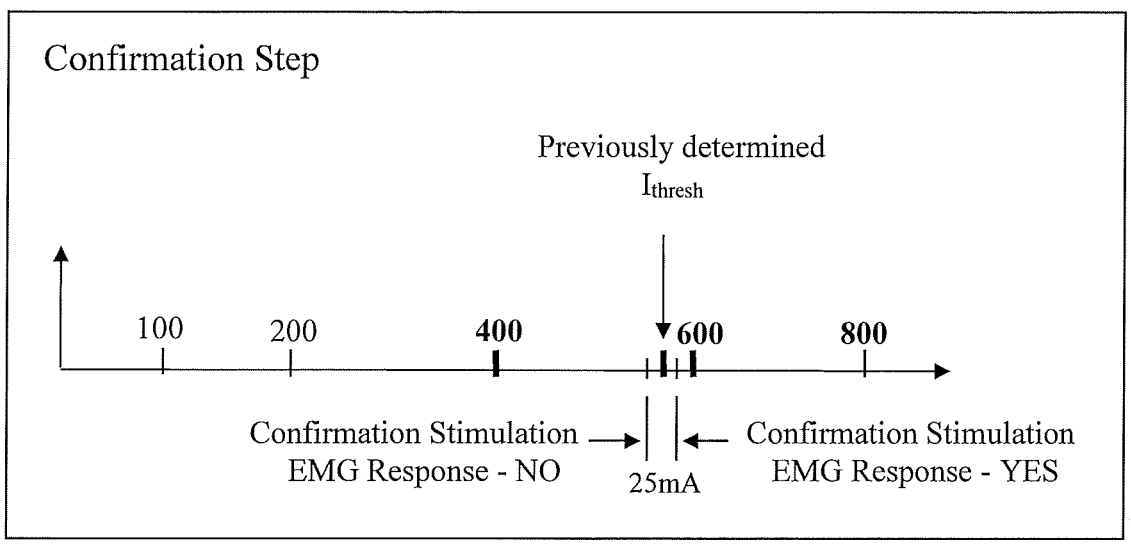
FIG. 21 is a graph illustrating the confirmation step employed by the algorithm to determine whether $I_{thresh}$ has changed from a previous determination.

FIG. 21 illustrates, by way of example only, a method employed by the MEP threshold hunting algorithm for confirming a previous threshold. The confirmation step attempts to ascertain whether $I_{thresh}$ has moved from its last known value. To do this, the algorithm applies two stimulation currents, one at or just above the threshold value and the other just below the threshold value. If the stimulation at or above $I_{thresh}$ recruits and the stimulation just below $I_{thresh}$ does not recruit, then the threshold has not moved and the algorithm may report that value as $I_{thresh}$ and proceed to process another channel. If the stimulation just below $I_{thresh}$ recruits, it may be concluded that $I_{thresh}$ has decreased and likewise if the stimulation at or just above $I_{thresh}$ fails to recruit, it may be concluded that $I_{thresh}$ has increased.

If $I_{thresh}$ cannot be confirmed, the algorithm enters the bracketing state. Rather than beginning the bracketing state from the minimum stimulation current, however, the bracketing state may begin from the previous $I_{thresh}$. The bracketing may advance up or down depending on whether $I_{thresh}$ has increased or decreased. By way of example only, if the previous value of $I_{thresh}$ was 400 mA, the confirmation step may stimulate at 400 mA and 375 mA. If the stimulation at 400 mA fails to evoke a significant response, it may be concluded that the $I_{thresh}$ has increased and the algorithm will bracket up from 400 mA. When the algorithm enters the bracketing state, the increment used in the confirmation step (ie. 25 mA in this example) is doubled. Thus, in this example, the algorithm stimulates at 450 mA. If the channel fails to recruit at this current level, the increment is doubled again (100 mA in this example) and the algorithm stimulates at 550 mA. This process is repeated until the maximum stimulation current is reached or the channel recruits, at which time the bisection function may be performed. If, during the confirmation step, the stimulation current just below the previously determined $I_{thresh}$ recruits, it may be concluded that $I_{thresh}$ for that channel has decreased and the algorithm may bracket down from that value (375 mA in this case). Thus, in this example, the algorithm would double the increment to 50 mA and stimulate at 325 mA. If the channel still recruits at this stimulation current, the increment is doubled again to 100 mA such that the algorithm stimulates at 225 mA. This process is repeated until the minimum stimulation current is reached or the channel fails to recruit, at which time the algorithm may perform the bisection function. When determining $I_{thresh}$ for multiple channels with previously determined $I_{thresh}$ values, this technique may be performed for each channel, in turn, in any order. Again stimulations may be omitted and the algorithm may begin processing a new channel before completing the algorithm for another channel, as described above.

Although the hunting algorithm is discussed herein in terms of finding $I_{thresh}$ (the lowest stimulation current that evokes a predetermined EMG response), it is contemplated that alternative stimulation thresholds may be useful in assessing the health of the spinal cord or nerve monitoring functions and may be determined by the hunting algorithm. By way of example only, the hunting algorithm may be employed by the system 10 to determine a stimulation voltage threshold, $Vstim_{thresh}$. This is the lowest stimulation voltage (as opposed to the lowest stimulation current) necessary to evoke a significant EMG response, $V_{thresh}$. Bracketing, bisection and monitoring states are conducted as described above for each active channel, with brackets based on voltage being substituted for the current based brackets previously described. Moreover, although described above within the context of MEP monitoring, it will be appreciated that the algorithms described herein may also be used for determining the stimulation threshold (current or voltage) for any other EMG related functions, including but not limited to bone integrity (e.g. pedicle screw test), nerve detection, and nerve root retraction.

According to one embodiment of the present invention, the surgical system 10 may perform the MEP function in either of two modes: Automatic mode and Manual mode. In one embodiment, these MEP modes are selectable from the drop-down function menu 104 of FIG. 4. In Automatic mode, the multi-channel MEP threshold hunting algorithm described above is utilized to determine a baseline $I_{thresh}$ for each channel, preferably prior to or in the early stages of a surgical procedure. It should be appreciated, however, that a new baseline $I_{thresh}$ may be determined at any time during the procedure at the option of the surgeon or other qualified operator. Having determined a baseline $I_{thresh}$ for each channel, subsequent monitoring may be performed as desired throughout the procedure and recovery period to obtain updated $I_{thresh}$ values for each channel. Each new determination of $I_{thresh}$ is compared by the surgical system 10 to the baseline $I_{thresh}$ for the appropriate channel. The difference ($\Delta I_{thresh}$) between the baseline $I_{thresh}$ and the new $I_{thresh}$ is calculated by the system 10 and the $\Delta I_{thresh}$ value is compared to predetermined "safe" and "unsafe" values. If $\Delta I_{thresh}$ is greater than the predetermined safe level, the user is alerted to a potential complication and action may be taken to avoid or mitigate the problem. The speed with which the multi-channel MEP threshold hunting algorithm is able to determine $I_{thresh}$ across all channels, and the simplicity with which the data communicated to the user may be interpreted, allows the user to increase the frequency of MEP monitoring conducted during a procedure without a concurrent increase in overall surgery time. This provides significant benefit to the patient by reducing the time intervals in between MEP monitoring episodes during which an injury to the spinal cord may go undetected.

Figure 22:
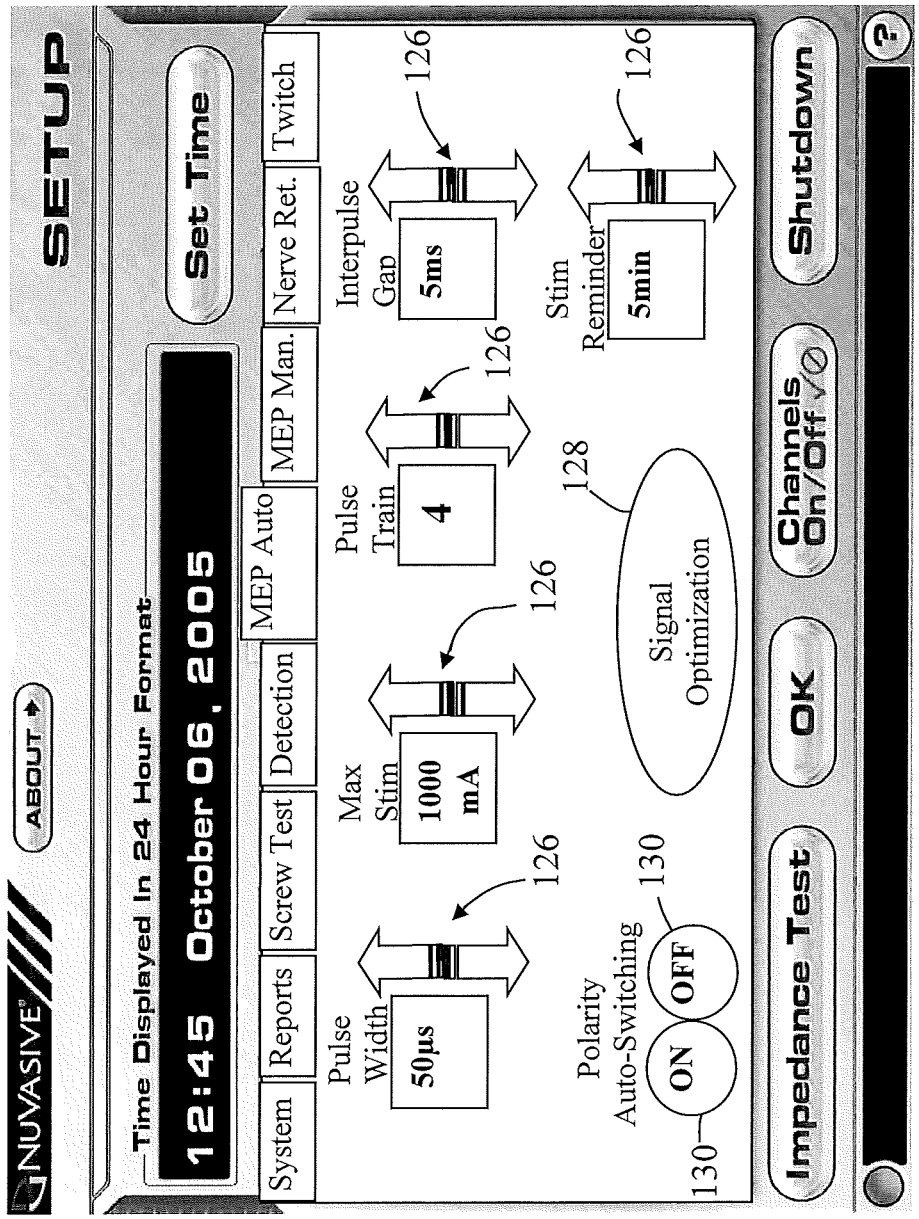
FIG. 22 is an exemplary screen display illustrating one embodiment of a MEP automatic mode setup screen according to the present invention.

In use, various features and parameters of the MEP function may be controlled and/or adjusted by the operator. In one example such control may be exercised from an "MEP Auto" mode setup screen, shown by way of example only in FIG. 22. Using this screen, the operator may turn different EMG channels on or off, set the date and time, conduct an impedance test to check the electrical connection between the EMG electrodes and the patient's skin, shutdown the system 10, and change one or more stimulation settings. Up and down control arrows 126 may be selected to increase or decrease the maximum allowable stimulation current (I), the pulse width (W), the number of pulses per stimulation signal (N), and the interpulse gap (G). MEP responses may be affected by a number of variables and the current level needed to evoke a significant response (i.e. $I_{thresh}$) may vary based on the parameters of the stimulation signal used. By varying the stimulation signal parameters, the operator may optimize the stimulation signal for each patient (e.g. find the signal parameters that result in the lowest $I_{thresh}$ values). In one embodiment, signal optimization may also be carried out automatically by the surgical system 10. Automatic signal optimization may be initiated by selecting a "signal optimization" tab 128, which will cause the surgical system 10 to perform a series of stimulations varying the different signal parameters until a signal configuration resulting in the lowest $I_{thresh}$ values is determined. If more than one pair of stimulation electrodes 23 have been arranged on the head, then signal optimization may be advantageous in determining which electrodes 23 generate a better response. It may also be advantageous to optimize the signal after any instance where the signal is not detected or otherwise deteriorates.

The polarity of the stimulation signal also has an effect on the MEP response. Positive phase stimulations may, for example, result in a lower $I_{thresh}$ values for muscles on the left side of the body than the right side of the body (or vice versa). To achieve the best MEP response values for all channels, it may be desirable to include stimulation signals of both positive and negative polarity. A polarity auto-switching feature may be controlled using on/off tabs 130. When polarity auto-switching is on, stimulation signals from MEP stimulator 21 alternate between a positive phase and a negative phase. The left and right sides of the brain may respond differently to positive and negative pulses. Each stimulation signal is used twice, once as a positive phase signal and once as a negative phase signal, before the hunting algorithm advances to the next stimulation current level. By way of example, if the algorithm begins stimulations at a minimum stimulation current of 100 mA, a first stimulation signal will include 1 to 8 positive phase pulses of 100 mA. A second stimulation signal will then include the same number of negative phase pulses of the same current, 100 mA. After stimulation results have been determined for the first current level using both polarities, the algorithm will stimulate at the next current level, in this case 200 mA, first with a positive phase signal followed by the negative phase signal. The algorithm will continue in this pattern until $I_{thresh}$ is determined for each channel. The order in which positive and negative phases are used is not important and may be reversed such that the first stimulation signal includes negative phase pulses and the second signal follows with positive phase pulses. When polarity auto-switching is turned off, the operator may select the polarity to be used from the MEP display screen (FIG. 23) or the stimulations may occur according to a default setting, which may be set as either positive or negative polarity.

The surgical system 10 includes the ability to remind the user to perform an MEP stimulation, which can be controlled from the setup screen. Using up and down control arrows 126, the operator may set and/or change a time interval for receiving stimulation reminders. After each MEP monitoring episode, the system 10 will initiate a timer corresponding to the selected time interval and, when the time has elapsed, a stimulation reminder will be activated. The stimulation reminder may include, by way of example only, any one of, or combination of, an audible tone, voice recording, screen flash, pop up window, scrolling message, or any other such alert to remind the operator to test MEP again.

Figure 23:
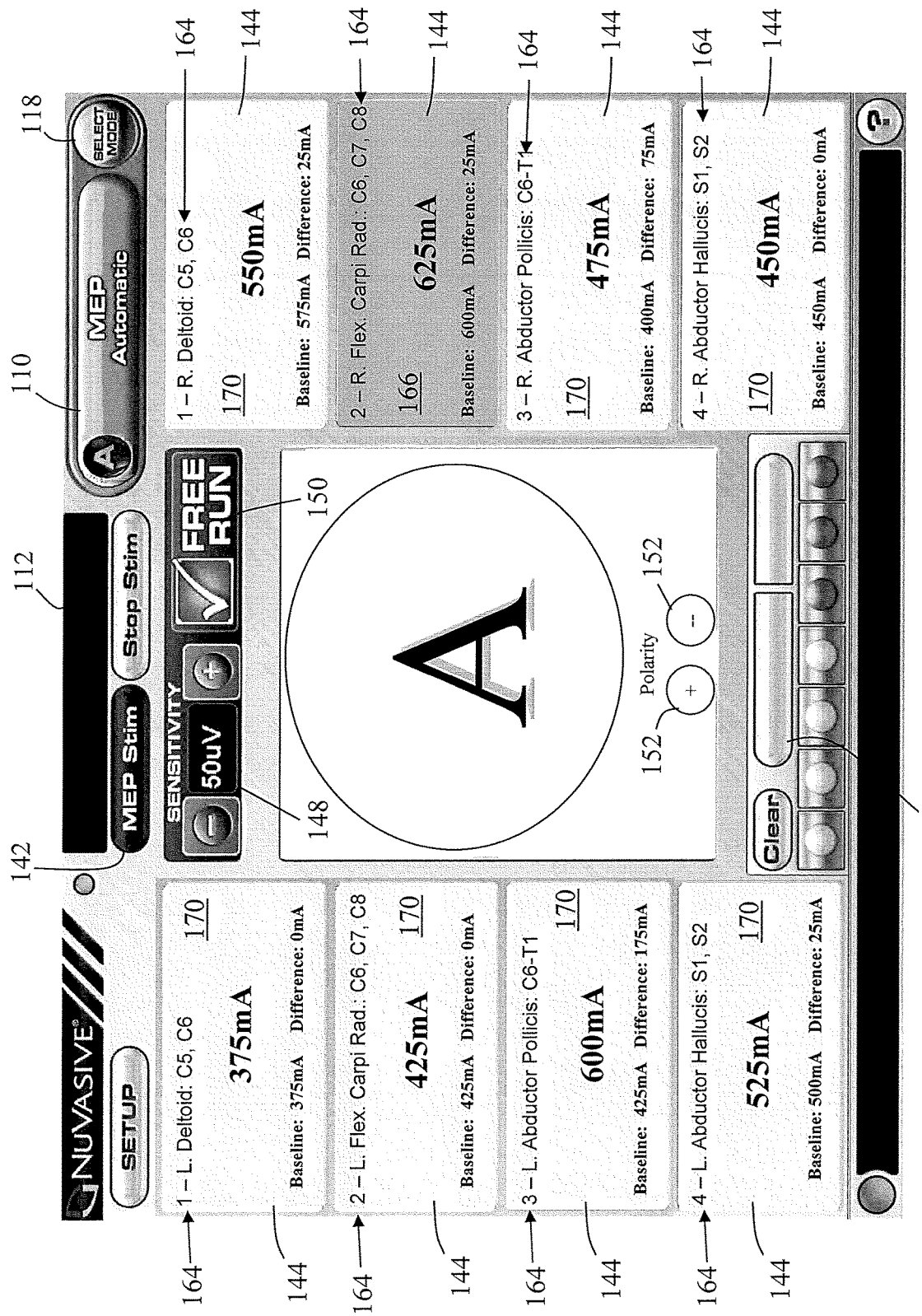
Figure 24:
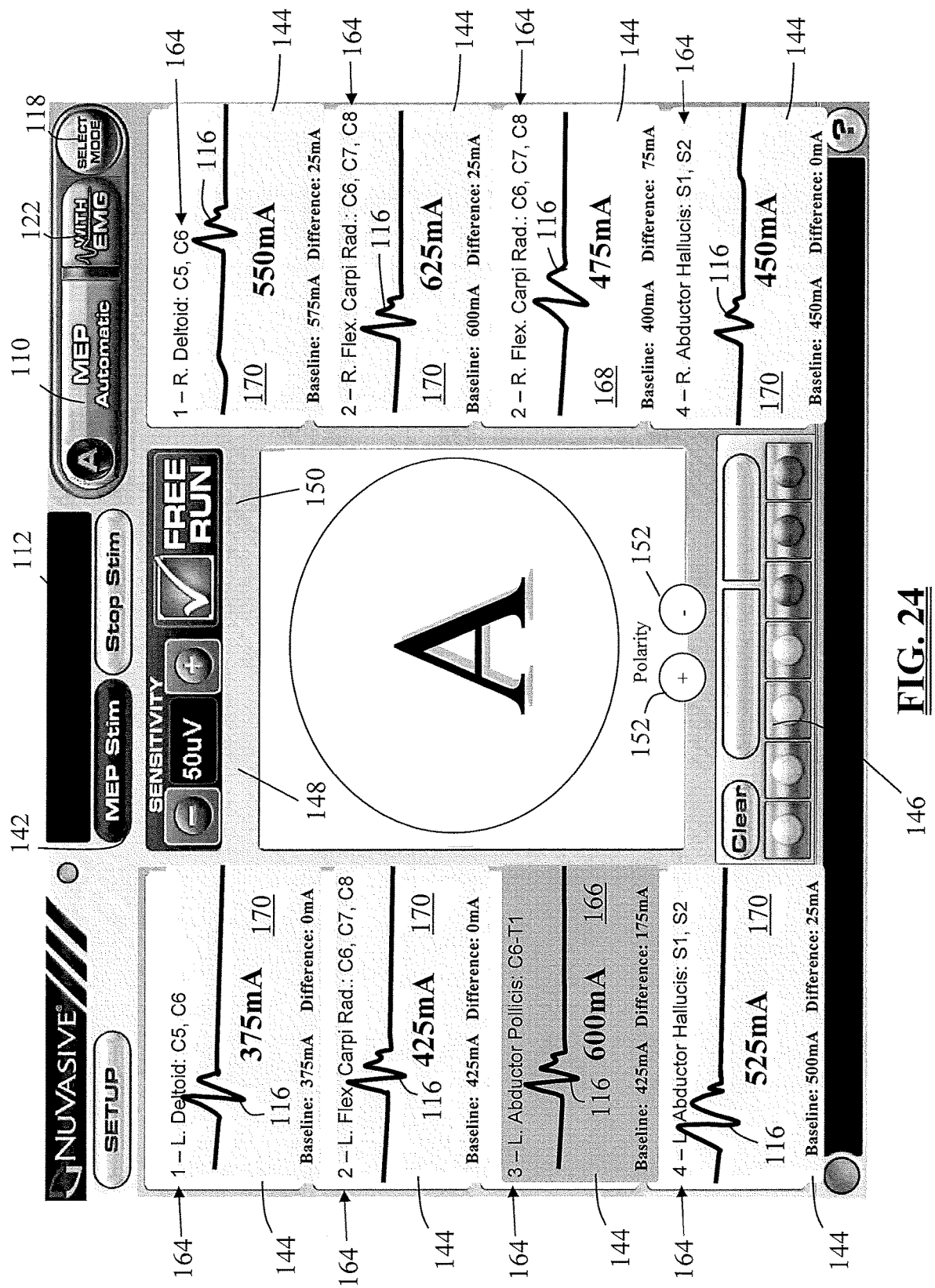

FIGS. 23-24 depict exemplary screen displays for automatic mode of the MEP function, one with alpha-numeric information only (FIG. 23) and one with alpha-numeric information along with optional EMG waveforms 116 (FIG. 24). A mode indicator tab 110 indicates that "MEP Automatic" is the selected mode. Polarity of the stimulation signal may be manually selected using the plus (+) and minus (−) polarity tabs 152. MEP stimulation may be initiated by selecting the stimulation start button 142 labeled (by way of example only) "MEP Stim." A stimulation bar 112 graphically depicts the stimulation current level. A channel window 144 is included for each EMG channel. The channel window 144 may display information including the channel number, myotome name, and associated spinal levels 164. Each channel window 144 may also display the baseline threshold, the most recent detected threshold value, and the difference between the two values. In the event the system 10 detects a significant difference ($\Delta I_{thresh}$) between the baseline threshold and the most recent threshold on a particular channel, the associated channel window 144 may preferably be highlighted with a predetermined color (e.g. red) to indicate the potential danger to the surgeon. Preferably, the stimulation results are displayed to the surgeon along with a color code so that the operator may easily comprehend the situation and avoid neurological impairment to the patient (e.g. red for "danger," yellow for "caution" and green for "safe"). In the example shown, the red is denoted with reference numeral 166, yellow is denoted with reference numeral 168, and green is denoted with reference numeral 170. In one embodiment of the MEP mode, set forth by way of example only, a green channel window 144 corresponds to a stimulation threshold change, $\Delta I_{thresh}$, of less than 25 mA, a yellow window denotes a stimulation threshold change of between 25-150 mA, and a red channel window 144 denotes a stimulation threshold change of greater than 150 mA. Annotation buttons 146 allow the surgeon to quickly annotate a threshold response with useful information that may not be automatically detectable by the system 10.

EMG sensitivity controls 148 and a Free-Run status control 150 are also provided on the screen. A check mark displayed in the free-run status control 150 indicates that free-run EMG mode is activated. When free-run is activated, the surgical system 10 continuously monitors EMG electrodes 18 for spontaneous nerve activity unless another mode, such as MEP, is active. Upon completion of an MEP episode, the surgical system 10 may automatically transition into free-run EMG monitoring, in which actual EMG waveforms are continuously displayed in real-time. In doing so, the user may be alerted to any nerve activity occurring unexpectedly. An audio pick-up (not shown) may also be provided as an optional feature according to the present invention. In some cases, when a nerve is stretched or compressed, it will emit a burst or train of spontaneous nerve activity. The audio pick-up is capable of transmitting sounds representative of such activity such that the surgeon can monitor this response on audio to help him or her determine if there has been stress to the nerve.

In manual MEP mode, the user simply selects a stimulation current and the system 10 determines whether or not the selected current evokes a predetermined EMG response. The user may be alerted to a potential complication if no response is detected from an EMG channel that had previously responded to a stimulation signal of the same or lesser amplitude. In one embodiment, set forth by way of example only, the user may determine for each channel a baseline stimulation current at which the stimulation signal evokes a response. Thereafter, the user may stimulate at each baseline and determine whether the corresponding channel still responds. Alternatively, a supramaximal current may be determined at which all channels show a response. Subsequent stimulations signals may be delivered at the same supramaximal current level and should continue to evoke a response. Subsequent absence of a response may be indicative of a problem with the spinal cord.

Figure 25:
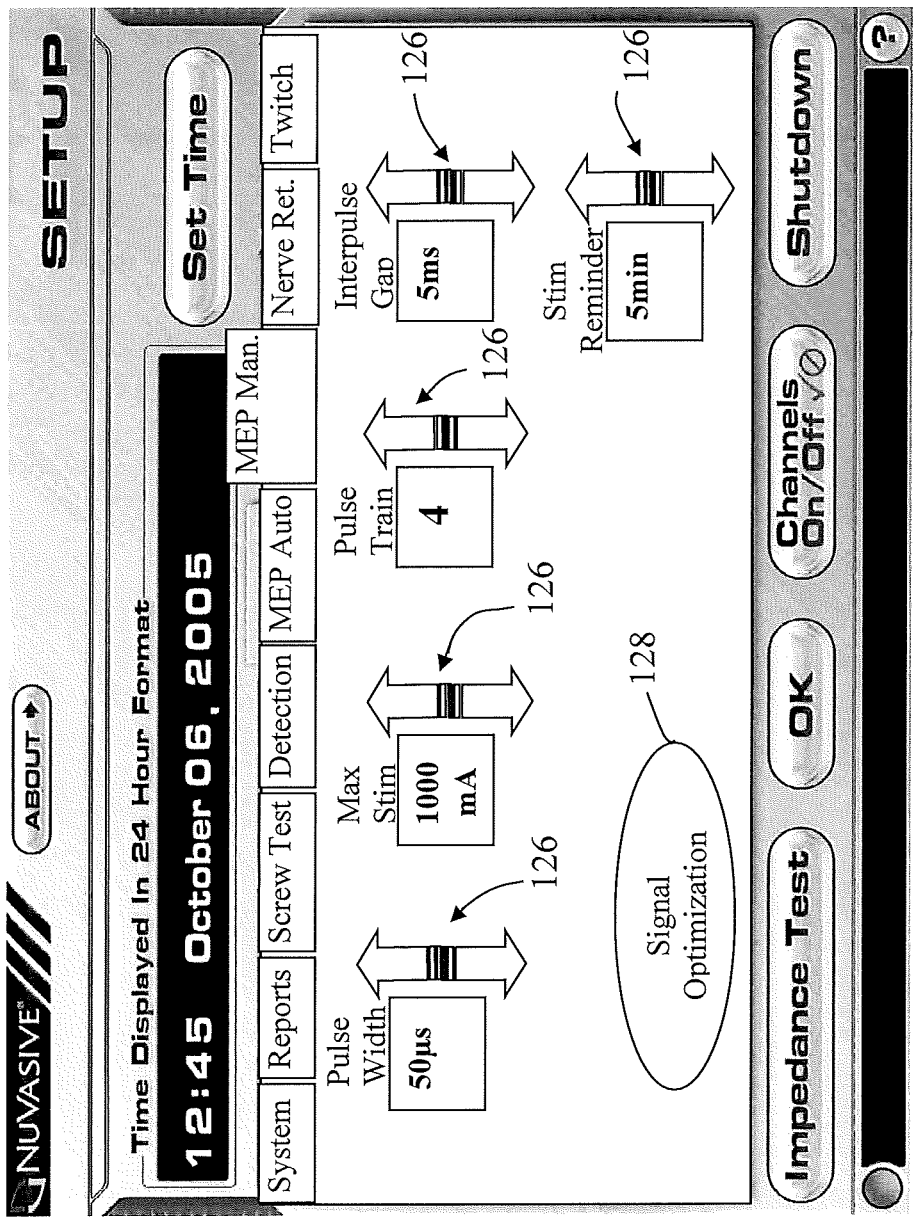
FIG. 25 is an exemplary screen display illustrating one embodiment of a MEP manual mode setup screen according to the present invention.

FIG. 25 shows, by way of example only, an exemplary setup screen for the MEP manual mode. In similar fashion to the setup screen previously described for "MEP Automatic" mode, the operator may turn different EMG channels on or off, set the date and time, conduct an impedance test to check the electrical connection between the EMG electrodes and the patient's skin, shutdown the system 10, and change one or more stimulation settings. Up and down control arrows 126 may be selected to increase or decrease the maximum allowable stimulation current (I), the pulse width (W), the number of pulses per stimulation signal (N), the interpulse gap (G), and a stimulation reminder time interval. By selecting the "signal optimization" tab 128, as described above, the system 10 will initiate a series of stimulation signals and determine an optimum configuration of stimulation signal parameters to obtain the best MEP responses.

Figure 26:
FIGS. 26-27 are exemplary screen displays illustrating various embodiments of the MEP manual mode function according to one aspect of the present invention.
Figure 27:
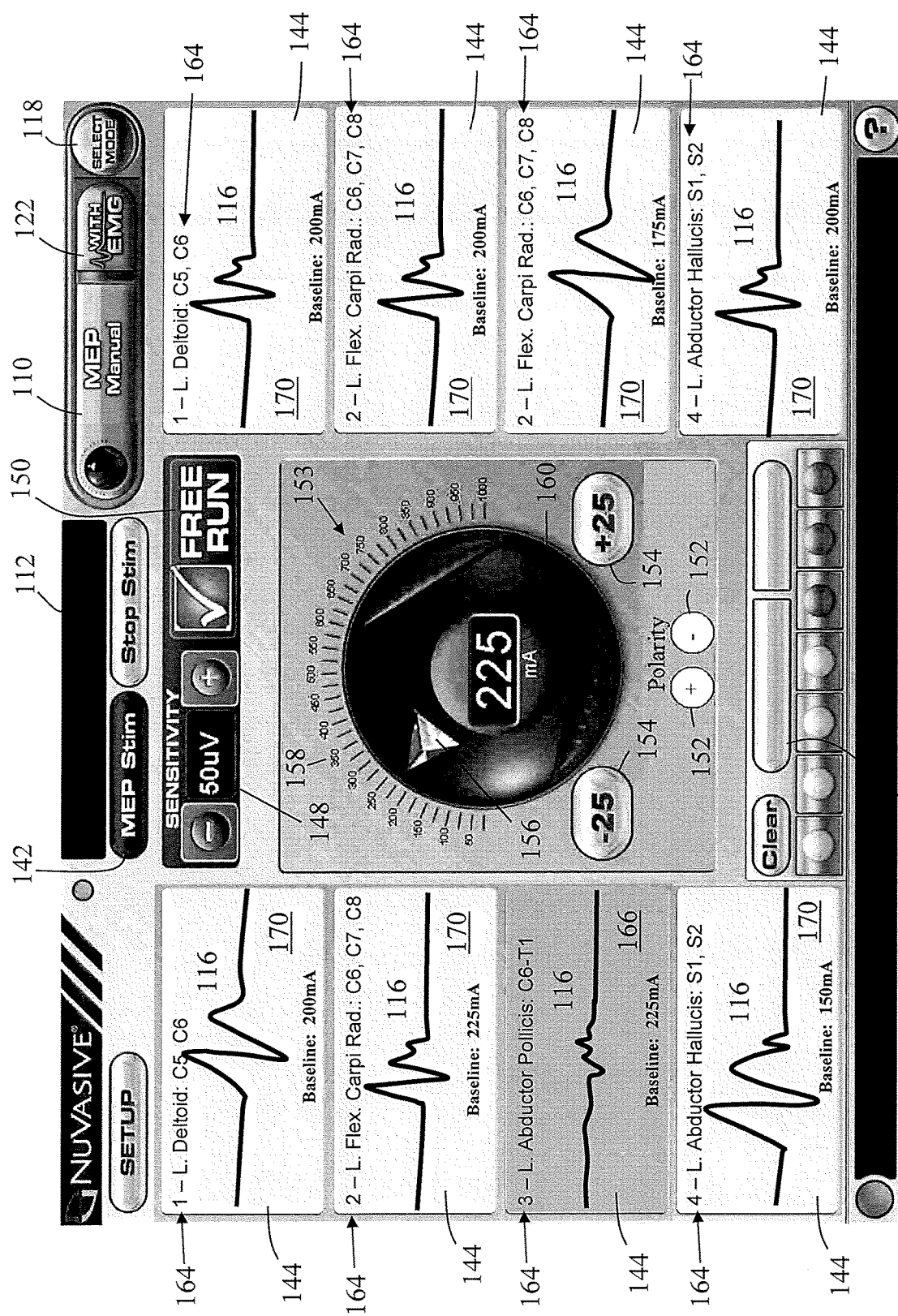

FIGS. 26-27 illustrate exemplary screen displays of "MEP Manual" mode, one with alpha-numeric information only (FIG. 26) and one with alpha-numeric information along with optional EMG waveforms 116 (FIG. 27). A mode indicator tab 110 indicates that "MEP Manual" mode is selected. An amplitude dial 153 is used to manually set the stimulation current. The amplitude setting may be increased or decreased in increments of 25 mA using the amplitude selection buttons 154 labeled (by way of example only) "+25" and "−25". More precise amplitude selections may be made by sweeping the dial indicator 156 around the dial face 158. The exact dial setting 160 is indicated in the center of the dial 153. Polarity controls 152 may be used to set the desired polarity of the stimulation signal. MEP stimulation may be initiated at the selected current amplitude shown in the dial setting 160 by pressing the stimulation start button 142 labeled (by way of example only) "MEP Stim." The stimulation bar 112 graphically depicts the stimulation current level. Each EMG channel includes a channel window 144. Provided in the channel window 144 is information including the channel number, myotome name, and associated spinal levels 164. Stimulation results are displayed in the form of "Yes" or "No" responses (or equivalent indicia, such as a "check" mark for yes and an "X" for no) indicated in the appropriate channel windows 144. If baselines were determined, the baseline values may also be shown in the appropriate channel windows 144. Channel windows 144 indicating a "No" response are preferably colored red (denoted 166) to clearly indicate to the operator the lack of response suggesting a potential complication. Channel windows indicating a "Yes" response are preferably colored green (denoted 170) to clearly indicate to the operator the presence of a response suggesting no potential problems. Annotation buttons 146 allow the surgeon to quickly annotate a stimulation response with useful information that may not be automatically detectable by the system 10. EMG sensitivity controls 148 and a Free-Run status control 150 are also provided on the screen.

Figure 28:
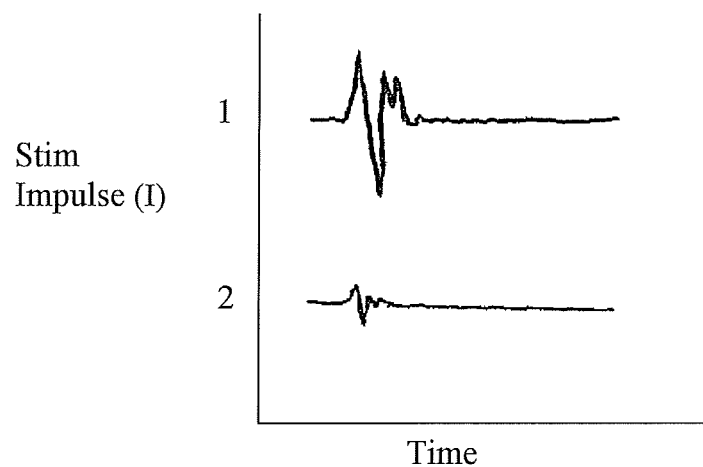
FIG. 28 is a graph illustrating a decrease in the EMG response amplitude demonstrating an additional method of assessing the health of the spinal cord and nerve pathways.
Figure 29:
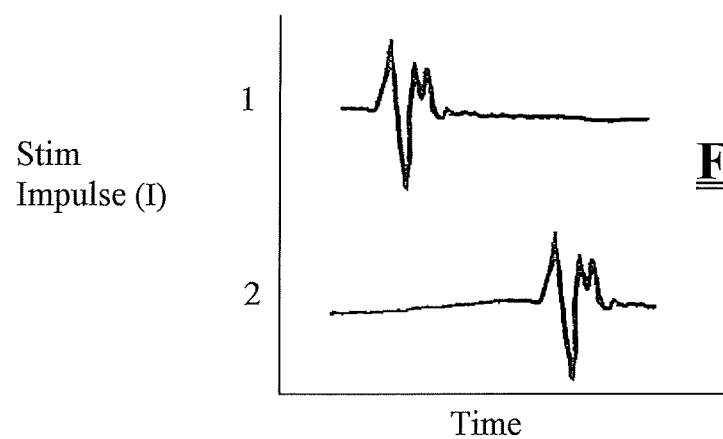
FIG. 29 is a graph illustrating an increase in the EMG response latency period demonstrating another method of assessing the health of the spinal cord.
Figure 30:
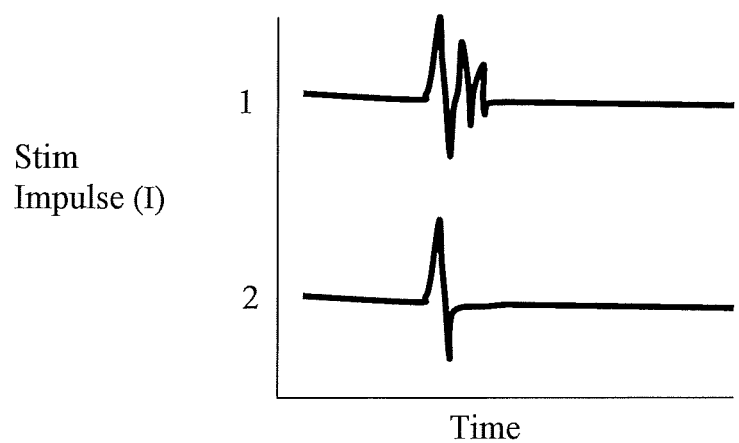
FIG. 30 is a graph illustrating a change in EMG response waveform morphology from a complex multiphasic waveform to a bi-phasic waveform demonstrating yet one more additional method for assessing the health of the spinal cord.

In addition to the MEP techniques described above, or instead of these techniques, the surgical system 10 is capable of monitoring spinal cord health via any number of different manners using additional data from the MEP test. For example, the system 10 may monitor changes in amplitude of the EMG responses as an indicator of spinal cord health. The system 10 may detect changes over time of the peak-to-peak voltage (i.e. amplitude of the EMG response) relative to a given stimulation signal current (shown in FIG. 28), which may be indicative of damage in spinal cord inhibiting signal transmission. The system 10 may measure the $V_{pp}$ response corresponding to a stimulation using the constant current, $I_{stim}$. The system 10 may then compare the $V_{pp}$ of the present reading to a proceeding or baseline reading taken in response to a stimulation signal of the constant $I_{stim}$. The difference between the present $V_{pp}$ value and the prior $V_{pp}$ value may then be communicated via the onscreen display 26. In one embodiment, "MEP Automatic" mode may be used initially to quickly determine a suitable $I_{stim}$ current. This may be accomplished by determining $I_{thresh}$ for each active channel using the multi-channel MEP threshold hunting algorithm. $I_{stim}$ may then preferably be selected with an amplitude slightly greater than the largest $I_{thresh}$. The surgical system 10 may also monitor spinal cord health by assessing the timing of the MEP response waveform. There is a characteristic delay from the time a stimulation pulse is delivered to the motor cortex to the time a corresponding muscle response is detected. This delay or latency period may be detected by the system 10. An increase in the latency period over successive measurements, as depicted in FIG. 29, may be a further indicator of problems with the stimulation signal transmission through the spinal cord. As such, the system 10 may detect an increase in latency with respect to a previously recorded baseline reading or the preceding reading, and the information may be conveyed to the operator via the display 26. The surgical system 10 may also monitor spinal cord health by assessing the morphology of an MEP response waveform. MEP response waveforms (EMG) are often complex polyphasic waves with several peaks. A baseline stimulation signal amplitude may be determined at which a polyphasic response is consistently produced. Subsequent changes to a bi-phasic or tri-phasic waveform, as illustrated in FIG. 30, in response to a stimulation signal of the same current may again be an indication of problems affecting the health of the spinal cord.

In a second broad aspect of the present invention, the surgical system 10 is capable of assessing the health of the spinal cord via SSEP monitoring. The system performs SSEP monitoring by stimulating peripheral sensory nerves that exit the spinal cord below the level of surgery and measuring the electrical action potential from electrodes located on the nervous system tract superior to the surgical target site. The neural electrical signal is then analyzed in relation to the stimulation pulse, resulting in quantitative information related to the health of the spinal cord, which is then conveyed to the surgeon via the display 26. SSEP stimulation may be conducted on the Posterior Tibial nerve with the electrical signal being recorded from any suitable location, including but not limited to the skin overlying the second cervical (C2) vertebrae or the skin of the scalp. Accordingly, a pair of peripheral nerve stimulation (PNS) electrodes 25 may be positioned on the skin above the Posterior Tibial nerve, located at the ankle, and recording electrodes 41 may be placed on the skin above the C2 vertebra. The stimulation pulse is delivered by the patient module 14, which is coupled to the PNS electrodes 25 via an accessory cable 30. Although SSEP stimulation and recording is discussed with respect to the Posterior Tibial nerve and C2 vertebra, it will be appreciated that SSEP stimulation may applied to any number of peripheral sensory nerves, including but not necessarily limited to the Ulnar and Median nerves in the wrist, as well as directly stimulating the spinal cord inferior to the expected level of potential damage. Likewise, it will be appreciated that the recording site may be located anywhere along the nervous system superior to the spinal level at risk during the procedure, including but not necessarily limited to any suitable location on the scalp.

When the peripheral sensory nerve is stimulated an electrical pulse ascends from the nerve to the spinal cord and up into the brain. Damage in the spinal cord can disrupt transmission of the signal up the cord, resulting in a weakened or delayed signal at the recording site. The surgical system 10 detects such disruptions by measuring the amplitude of the stimulation signal waveform when it reaches the recording site, as well as the latency period (time signal takes to travel from the stimulation site to the recording site). The system 10 compares amplitude measurements to a previously recorded baseline amplitude or the preceding measurement, and the difference between them is viewed on the display 26. Similarly, latency measurements are compared to a previously recorded baseline latency or the preceding measurement and the difference value is shown on the display 26. A decrease in amplitude or an increase in latency may alert the surgeon to damage in the spinal cord and corrective measures may be taken to avoid or mitigate such damage.

Figure 31:
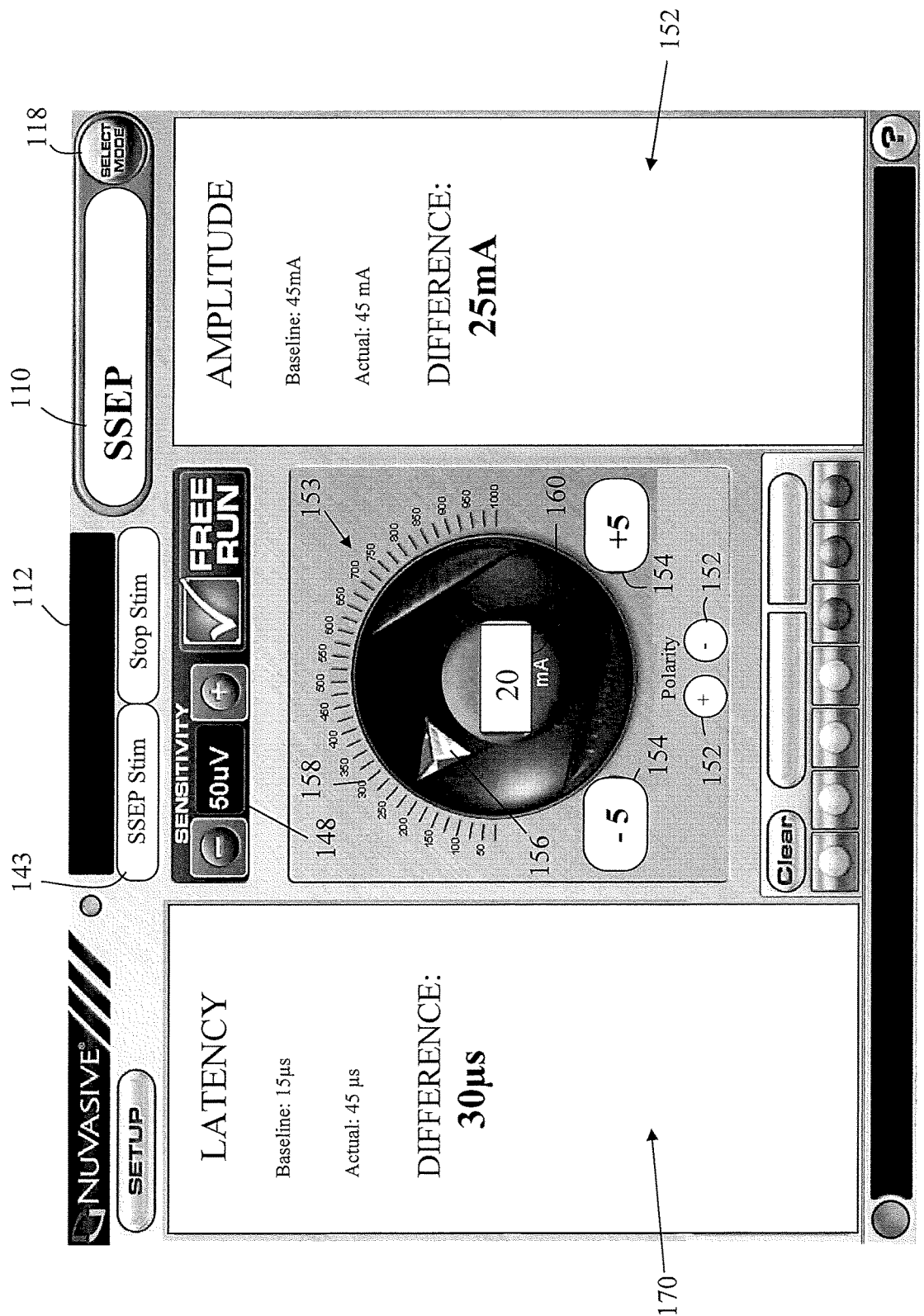
FIG. 31 is an exemplary screen display illustrating one embodiment of the SSEP function of the present invention.
Figure 32:
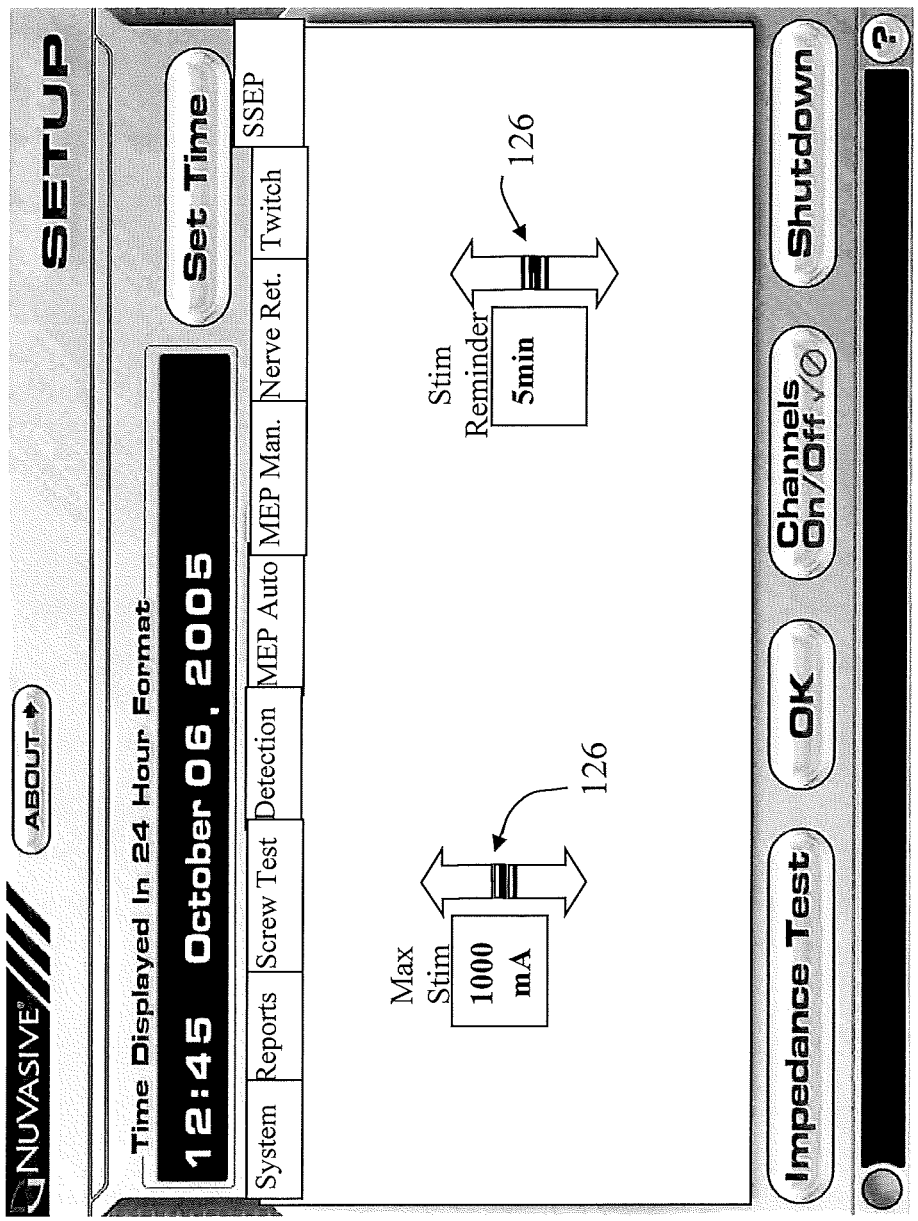
FIG. 32 is an exemplary screen display illustrating one embodiment of a SSEP setup screen according to one aspect of the present invention.

FIG. 31 is an exemplary illustration of an onscreen display for the SSEP mode. A mode indicator tab 110 indicates that SSEP is the selected mode. An amplitude dial 153 is used to set the stimulation current. The amplitude setting may be increased or decreased in increments of 5 mA using the amplitude selection buttons 154 labeled (by way of example only) "+5" and "−5". More precise amplitude selections may be made by sweeping the dial indicator 156 around the dial face 158. The precise dial setting 160 is indicated in the center of the dial 153. Polarity controls 152 may be used to set the desired polarity of the stimulation signal. SSEP stimulation may be initiated at the selected current amplitude shown in the dial setting 160 by pressing the SSEP stimulation start button 143 labeled (by way of example only) "SSEP Stim." A stimulation bar 112 graphically depicts the stimulation current level. By way of example only, the SSEP information communicated to the user in the window 170 may relate to the changes in latency and amplitude between baseline values and the present reading or test. In the example shown, the latency information includes baseline (15 μs), present reading (19 μs), and difference (4 μs), while the amplitude information includes baseline (12 μv), present reading (11 μv), difference (1 μv), and the percentage change (8%). This information may be interpreted as being indicative of a problem with the neural pathways being tested. For example, a reduction in amplitude of 50% between baseline and a present reading is indicative of a potential problem with the neural pathway being tested. The numerical results may be accompanied by the same color code discussed above. Red is used when the decrease in amplitude or increase in latency is within a predetermined unsafe level. Green indicates that the measured increase or decrease is within a predetermined safe level. Yellow is used for measurements that are between the predetermined unsafe and safe levels. FIG. 32 depicts, by way of example only, a setup screen for SSEP. Using this screen, the operator may change the stimulation current level using up and down control arrows 126, set the date and time, conduct an impedance test to check the electrical connection between the recording electrodes and the patients skin, and shutdown the system 10.

In a third significant aspect of the present invention, the surgical system 10 may conduct other nerve monitoring functions, including but not necessarily limited to, neuromuscular pathway assessments to ensure that muscle relaxants, paralytic agents, and/or anesthetics are no longer affecting the neuromuscular pathway (Twitch Test), bone integrity testing (e.g. Pedicle Screw Test), nerve proximity testing (Detection), and nerve pathology monitoring (Nerve Root Retraction). These additional functions have been described in detail in the NeuroVision Applications referenced above, the entire contents of which are expressly incorporated by reference as if set forth herein in their entirety, and will thus be described here only briefly. In similar fashion to the MEP function discussed above, the system 10 conducts nerve monitoring functions by electrically stimulating a nerve via one or more stimulation electrodes positioned on the surgical accessories 32, monitoring the corresponding muscle response of muscles innervated by the nerve, and analyzing the muscle response in relation to the stimulation signal to determine one of neuromuscular pathway function, bone integrity, nerve proximity, and nerve pathology. In a preferred embodiment, EMG monitoring may be conducted on the same muscle groups monitored for the MEP function, as illustrated above in Tables 2, 3, 4. In this manner, the EMG electrodes 18 need be placed only one time, prior to or at the beginning of the surgery, and may be used to monitor EMG responses for all the various functions of the system 10.

The surgical system 10 performs neuromuscular pathway (NMP) assessments (Twitch Test) by electrically stimulating a peripheral nerve via PNS electrodes 25 placed on the skin over the nerve or by direct stimulation of a spinal nerve using a surgical accessory such as balled-tipped test probe 36. Evoked responses from the muscles innervated by the stimulated nerve are detected and recorded, the results of which are analyzed and a relationship between at least two responses or a stimulation signal and a response is identified. The identified relationship provides an indication of the current state of the NMP. The identified relationship may include, but is not necessarily limited to, one or more of magnitude ratios between multiple evoked responses and the presence or absence of an evoked response relative to a given stimulation signal or signals. Details of the test indicating the state of the NMP and the relative safety of continuing on with nerve testing are conveyed to the surgeon via the screen display 26.

The surgical system 10 may test the integrity of pedicle holes (during and/or after formation) and/or screws (during and/or after introduction). The screw test probe 36 is placed in the screw hole prior to screw insertion or placed on the installed screw head and a stimulation signal is applied. The insulating character of bone will prevent the stimulation current, up to a certain amplitude, from communicating with the nerve, thus resulting in a relatively high $I_{thresh}$, as determined via the basic threshold hunting algorithm described above. However, in the event the pedicle wall has been breached by the screw or tap, the current density in the breach area will increase to the point that the stimulation current will pass through to the adjacent nerve roots and they will depolarize at a lower stimulation current, thus $I_{thresh}$ will be relatively low. In an alternative embodiment, screw test probe 36 may be replaced with an electric coupling device 42, 52 which may be utilized to couple a surgical tool, such as for example, a tap member 72 or a bone awl 74, to the surgical system 10. In this manner, a stimulation signal may be passed through the surgical tool and screw testing can be performed while the tool is in use. Thus, screw testing may be performed during pilot hole formation by coupling the bone awl 74 to the surgical system 10 and during pilot hole preparation by coupling the tap 72 to the system 10. Likewise, by coupling a pedicle screw to the surgical system 10 (such as via pedicle screw instrumentation), screw testing may be performed during screw introduction.

The surgical system 10 may perform nerve proximity testing (Detection) to ensure safe and reproducible access to surgical target sites. Using the surgical access components 62-66, the system 10 detects the existence of neural structures before, during, and after the establishment of an operative corridor through (or near) any of a variety of tissues having such neural structures which, if contacted or impinged, may otherwise result in neural impairment for the patient. The surgical access components 62-66 are designed to bluntly dissect the tissue between the patient's skin and the surgical target site. Cannulae or dilators of increasing diameter, which are equipped with one or more stimulating electrodes, are advanced towards the target site until a sufficient operating corridor is established. As the cannulae or dilators are advanced to the target site electrical stimulation signals are emitted via the stimulation electrodes. The stimulation signal will stimulate nerves in close proximity to the stimulation electrode and the corresponding EMG response is monitored. As a nerve gets closer to the stimulation electrode, the stimulation current ($I_{stim}$) required to evoke a muscle response decreases. $I_{thresh}$ is calculated, using the basic threshold hunting algorithm described above, providing a measure of the communication between the stimulation signal and the nerve and thus giving a relative indication of the proximity between access components and nerves.

Additional and/or alternative surgical access components such as, by way of example only, a tissue retraction assembly 70 (FIG. 1) may be coupled to the system 10 and employed to provide safe and reproducible access to a surgical target site. Tissue retraction assembly 70 and various embodiments and uses thereof have been shown and described in the above referenced co-pending and commonly assigned U.S. patent application Ser. No. 10/967,668, entitled "Surgical Access System and Related Methods," filed on Oct. 18, 2004, the entire contents of which are expressly incorporated by reference as if set forth herein in their entirety.

The surgical system 10 preferably accomplishes neural pathology monitoring via the Nerve Retractor function, specifically by determining a baseline stimulation threshold with direct contact between the nerve retractor 76 and the nerve, prior to retraction. Subsequent stimulation thresholds are determined during retraction and they are compared to the baseline threshold. Significant changes in the stimulation threshold may indicate potential trauma to the nerve caused by the retraction and are displayed to the user on the display 26. An increase in $I_{thresh}$ over time is an indication that the nerve function is deteriorating and retraction should be reduced or stopped altogether to prevent permanent damage.

Figure 33:
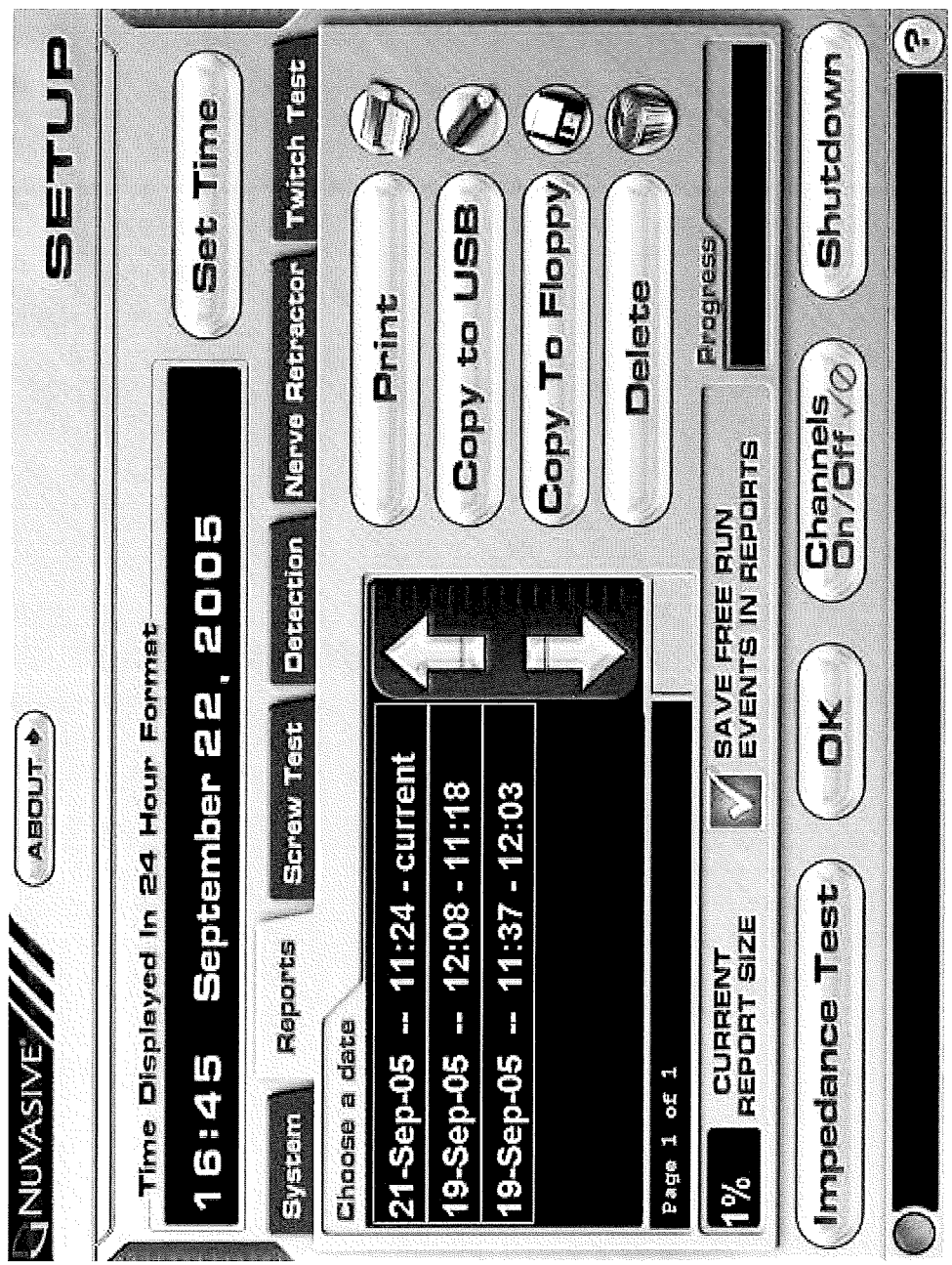
FIG. 33 is an exemplary screen display illustrating a method of generating a surgical report according to one embodiment of the present invention.
Figure 34:
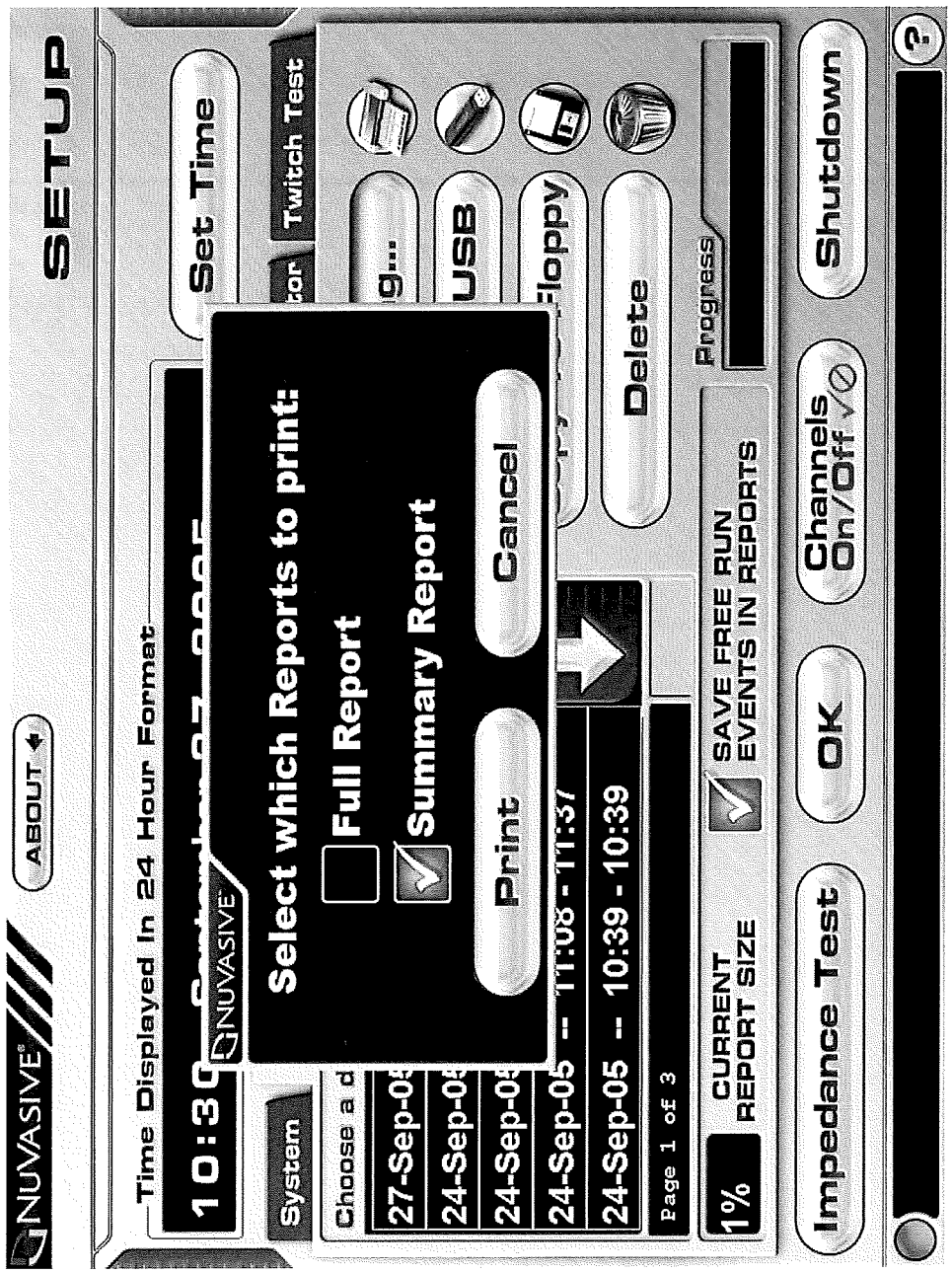
FIG. 34 is an exemplary screen display illustrating a method of selecting between a full surgical report or a summary surgical report according to one embodiment of the present invention.
Figure 35C:
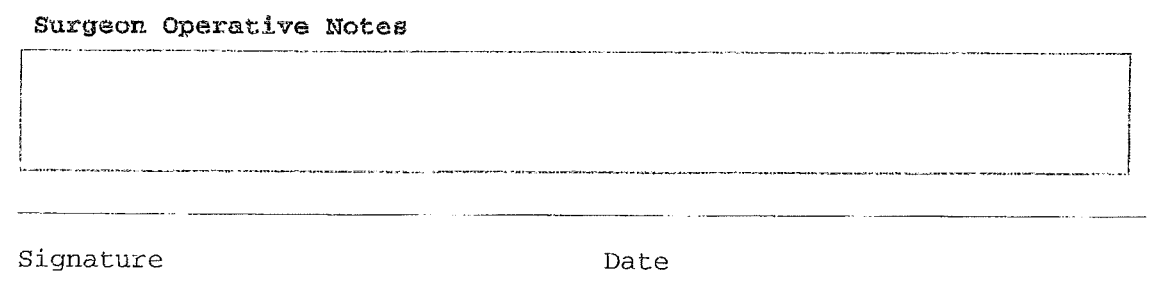

With reference to FIG. 33, the stimulation results, including annotations, may be compiled in a surgical report chronicling all nerve monitoring functions conducted during the procedure. In one embodiment the report may be printed immediately from one or more printers located in the operating room or copied to any of a variety of memory devices known in the prior art, such as, by way of example only, a floppy disk, or USB memory device. The system 10 may generate either a full report or a summary report depending the particular needs of the user, who may select one or both using the GUI screen display 26, as illustrated in FIG. 34. FIGS. 35A-35C are an exemplary representation of a summary report generated by system 10. The summary report includes space for patient, physician, and procedural information and surgeon operative notes along with the stimulation results. The stimulation results, including any annotated data, are preferably displayed in chronological order for each function. FIGS. 36A-36E are an exemplary representation of a full report generated by the system 10. The full report also includes space for patient and physician information and surgeon operative notes. The full stimulation results are displayed in chronological order regardless of the particular function.

The control unit 12 is configured to monitor the system status throughout its use. In the event the control unit 12 detects an aberration an error log is created in which the details of the error are described and stored to assist in later troubleshooting and system correction. To service the system 10, the error logs may be accessed directly from the control unit 12 hardware and software. In addition, error logs may be downloaded onto any of a number of suitable media to facilitate data transfer between remote locations. By way of example only, the error logs may be downloaded to a USB memory device, floppy disk, CD, or DVD. By way of further example, the error logs may be downloaded onto a network and transmitted to remote locations via the Internet or other data transfer systems.

It will be readily appreciated that various modifications may be undertaken, or certain steps or algorithms omitted or substituted, without departing from the scope of the present invention. By way of example only, several alternative methods will now be described. Rather than identifying the stimulation current threshold ($I_{Thresh}$) based on a predetermined $V_{Thresh}$ it is also within the scope of the present invention to determine $I_{Thresh}$ via linear regression. This may be accomplished via, by way of example only, the linear regression technique disclosed in commonly owned and co-pending U.S. patent application Ser. No. 09/877,713, filed Jun. 8, 200 and entitled "Relative Nerve Movement and Status Detection System and Methods," the entire contents of which is hereby expressly incorporated by reference as if set forth in this disclosure in its entirety.

Additionally, the nerve pathology monitoring function described above may be employed for the purpose of monitoring the change, if any, in peripheral nerves during the course of the procedure. This may be accomplished by positioning additional stimulation electrodes anywhere on a surgical accessory that is likely to come in contact with a peripheral nerve during a surgical procedure. Recruitment curves or other data can be generated and assessed in the same fashion described above.

Moreover, although described with reference to the surgical system 10, it will be appreciated as within the scope of the invention to perform MEP and SSEP monitoring as described herein with any number of different neurophysiology based testing, including but not limited to the "NIM SPINE" testing system offered by Medtronic Sofamor Danek, Inc.

While this invention has been described in terms of a best mode for achieving this invention's objectives, it will be appreciated by those skilled in the art that variations may be accomplished in view of these teachings without deviating from the spirit or scope of the present invention. For example, the present invention may be implemented using any combination of computer programming software, firmware or hardware. As a preparatory step to practicing the invention or constructing an apparatus according to the invention, the computer programming code (whether software or firmware) according to the invention will typically be stored in one or more machine readable storage mediums such as fixed (hard) drives, diskettes, optical disks, magnetic tape, semiconductor memories such as ROMs, PROMs, etc., thereby making an article of manufacture in accordance with the invention. The article of manufacture containing the computer programming code is used by either executing the code directly from the storage device, by copying the code from the storage device into another storage device such as a hard disk, RAM, etc. or by transmitting the code on a network for remote execution. As can be envisioned by one of skill in the art, many different combinations of the above may be used and accordingly the present invention is not limited by the specified scope.

What is claimed is:

1. A method for performing neurophysiologic assessments during surgery, comprising:
providing a signal to transmit a first set of electrical stimulation signals and a second set of electrical stimulation signals to the motor cortex of a patient via a stimulator, each of said first and second sets of electrical stimulation signals including stimulation signals having different electrical current amplitude;
receiving evoked motor evoked potential response data from at least one sensor, wherein the at least one sensor is configured to detect at least one motor evoked potential response evoked by the first and second sets of electrical stimulation signals;
determining a first lowest stimulation current amplitude for a first channel from the first set of electrical stimulation signals that evokes a motor evoked potential response greater than a threshold level, wherein the first channel is associated with a first sensor of the at least one sensor;
determining a second lowest stimulation current amplitude for a second channel from the second set of electrical stimulation signals that evokes a motor evoked potential response greater than said threshold level, wherein the second channel is associated with a second sensor of the at least one sensor, wherein determining the second lowest stimulation current amplitude is based at least in part on a determination of the lowest stimulation signal amplitude of the first set of electrical stimulation signals that recruited on the second channel and the highest stimulation signal amplitude of the first set of electrical stimulation signals that did not recruit on the second channel; and
displaying an onscreen assessment of a spinal cord health status based on at least one of (i) the determination of the first lowest stimulation current amplitude and (ii) the determination of the second lowest stimulation current amplitude.

2. The method of claim 1, wherein each of the first and second sets of electrical stimulation signals comprises a predetermined number of pulses separated by an interpulse gap, each pulse having a pulse width.

3. The method of claim 2, wherein the number of pulses ranges from 1 to 8 monophasic pulses, the interpulse gap ranges from 1 millisecond to 10 milliseconds, and the pulse width ranges from 50 microseconds to 400 microseconds.

4. The method of claim 3, wherein the monophasic pulses are positive phases pulses for all stimulation signals in the first and second sets of electrical stimulation signals.

5. The method of claim 2, wherein each of the first and second sets of electrical stimulation signals have amplitudes within a range from 0 milliamps to 1000 milliamps.

6. The method of claim 2, further comprising:
optimizing at least one stimulation signal from the first and second sets of electrical stimulation signals at least one of before conducting a neurophysiologic assessment of the spinal cord of the patient and after a response to the stimulation signal stops being detected during a neurophysiologic assessment of the spinal cord of the patient.

7. The method of claim 6, wherein optimizing the at least one stimulation signal comprises modifying at least one of the predetermined number of pulses, the interpulse gap, the pulse width, and the current level before the neurophysiologic assessment of the spinal cord.

8. The method of claim 1, further comprising:
providing a second signal to transmit a third set of electrical stimulation signals to one or more nerves within the patient via a second stimulator;
receiving evoked neuromuscular response data from the at least one sensor in response to the third set of stimulation signals,
determining a status of at least one of bone integrity, nerve direction, nerve pathology, and neuromuscular pathway integrity by identifying a relationship between a third lowest stimulation current amplitude from the third set of electrical stimulation signals that evokes a neuromuscular response greater than a predefined threshold; and
displaying the status of the at least one of bone integrity, nerve direction, nerve pathology, and neuromuscular pathway integrity.

9. The method of claim 1, wherein determining at least one of the first lowest stimulation current amplitude and the second lowest stimulation current amplitude further comprises:
establishing a bracket within which at least one of the first lowest stimulation current amplitude and the second lowest stimulation current amplitude is contained; and
successively bisecting the bracket until at least one of the first lowest stimulation current amplitude and the second lowest stimulation current amplitude is determined within a specified accuracy.

10. The method of claim 1, wherein providing the signal to transmit the first and second sets of electrical stimulation signals to the motor cortex of the patient occurs after receiving a start signal from a bite-block positioned within the patient's mouth, wherein the bite-block contains at least one electrode configured to initiate the start signal.

11. A method for performing neurophysiologic assessments during surgery, comprising:
providing a signal to transmit a first set of electrical stimulation signals to the motor cortex of a patient to perform motor evoked potential monitoring, a second set of electrical stimulation signals to the motor cortex of the patient to perform the motor evoked potential monitoring, and a third set of electrical stimulation signals to one or more peripheral nerves within the patient to perform somatosensory evoked potential monitoring;
receiving data from a plurality of sensors configured to detect one or more responses to the first, second, and third sets of electrical stimulation signals;
determining a first lowest stimulation current amplitude from the first set of electrical stimulation signals that evokes a motor evoked potential response greater than a first threshold level;
determining a second lowest stimulation current amplitude from the second set of electrical stimulation signals that evokes a corresponding neuromuscular response greater than a second threshold level, wherein determining the second lowest stimulation current amplitude is based at least in part on a determination of the lowest stimulation signal amplitude of the first set of stimulation signals that recruited and the highest signal amplitude of the first set of electrical stimulation signals that did not recruit;
determining a third lowest stimulation current amplitude from the third set of electrical stimulation signals delivered that evokes a corresponding neuromuscular response greater than a third threshold level;

displaying an onscreen assessment of a spinal cord health status based on at least one of (i) the determination of the first lowest stimulation current amplitude and (ii) the determination of the second lowest stimulation current amplitude; and displaying an onscreen assessment of at least one of nerve direction, nerve pathology, and neuromuscular pathway integrity status based on the determination of the third lowest stimulation current amplitude.

12. The method of claim 11, wherein each stimulation signal of the first set of electrical stimulation signals comprises a predetermined number of pulses separated by an interpulse gap, each pulse having a pulse width.

13. The method of claim 12, wherein the number of pulses ranges from 1 to 8 monophasic pulses, the interpulse gap ranges from 1 millisecond to 10 millisecond, the pulse width ranges from 50 microseconds to 400 microseconds and the respective current level falls within a range from 0 milliamps to 1000 milliamps.

14. The method of claim 13, wherein the monophasic pulses are positive phase pulses for all stimulation signals of the first set of electrical stimulation signals.

15. The method of claim 11, further comprising:
optimizing parameters of the first set of stimulation signals at least one of prior to performing the motor evoked potential monitoring and after a response to the first set of electrical stimulation signals stops being detected during the motor evoked potential monitoring.

16. The method of claim 15, wherein optimizing parameters of the first set of stimulation signals comprises modifying at least one of the number of pulses, the inter pulse gap, the pulse width, and the respective current level for each of the stimulation signals of the first set of electrical stimulation signals before performing the motor evoked potential monitoring.

17. The method of claim 11, wherein the first set of electrical stimulation signals includes a first electrical stimulation signal having a first stimulation current amplitude and a second electrical stimulation signal having a second stimulation current amplitude different from the first electrical current amplitude, wherein the second set of electrical stimulation signals includes a third electrical stimulation signal having a third stimulation current amplitude and a fourth electrical stimulation signal having a fourth stimulation current amplitude different from the third electrical current amplitude.

18. An apparatus for performing neurophysiologic assessments during surgery, wherein the apparatus comprises:

a control unit that includes a display and computer hardware, wherein the computer hardware is configured to:

cause a signal to transmit a first set of electrical stimulation signals and a second set of electrical stimulation signals to the motor cortex of a patient, each of said first and second sets of electrical stimulation signals including stimulation signals having different electrical current amplitude;

receive evoked motor evoked potential response data from at least one sensor, wherein the at least one sensor is configured to detect at least one motor evoked potential response evoked by the first and second sets of electrical stimulation signals;

determine a first lowest stimulation current amplitude for a first channel from the first set of electrical stimulation signals that evokes a motor evoked potential response greater than a threshold level, wherein the first channel is associated with a first sensor of the at least one sensor;

determine a second lowest stimulation current amplitude for a second channel from the second set of electrical stimulation signals that evokes a motor evoked potential response greater than said threshold level, wherein the second channel is associated with a second sensor of the at least one sensor, wherein determining the second lowest stimulation current amplitude is based at least in part on a determination of the lowest stimulation signal amplitude of the first set of stimulation signals that recruited on the second channel and the highest stimulation signal amplitude of the first set of stimulation signals that did not recruit on the second channel; and provide instructions to display at the display an onscreen assessment of a spinal cord health status based on at least one of (i) the determination of the first lowest stimulation current amplitude and (ii) the determination of the second lowest stimulation current amplitude.

19. The apparatus of claim 18, wherein each of the first and second sets of electrical stimulation signals comprises a predetermined number of pulses separated by an interpulse gap, each pulse having a pulse width.

20. The apparatus of claim 18, wherein the number of pulses ranges from 1 to 8 monophasic pulses, the interpulse gap ranges from 1 millisecond to 10 milliseconds, and the pulse width ranges from 50 microseconds to 400 microseconds.

* * * * *